(12) United States Patent
Kennedy

(10) Patent No.: US 8,577,013 B1
(45) Date of Patent: Nov. 5, 2013

(54) AUTOMATIC COMMUNICATIONS FORWARDING TO DISPLACED EMPLOYEES

(75) Inventor: James Lehr Kennedy, Columbus, OH (US)

(73) Assignee: West Corporation, Omaha, NE (US)

(*) Notice: Subject to any disclaimer, the term of this patent is extended or adjusted under 35 U.S.C. 154(b) by 0 days.

(21) Appl. No.: 13/346,801

(22) Filed: Jan. 10, 2012

Related U.S. Application Data

(60) Provisional application No. 61/431,157, filed on Jan. 10, 2011.

(51) Int. Cl.
*H04M 3/42* (2006.01)
*H04M 7/00* (2006.01)
*H04M 3/00* (2006.01)
*H04M 5/00* (2006.01)

(52) U.S. Cl.
USPC ............ 379/212.01; 379/211.02; 379/221.01; 379/221.02; 379/265.11; 379/265.12

(58) Field of Classification Search
USPC .................... 379/211.02, 265.11, 265.1, 219, 379/221.01, 221.02, 212.01, 265.12, 379/201.01; 706/47
See application file for complete search history.

(56) References Cited

U.S. PATENT DOCUMENTS

| | | | |
|---|---|---|---|
| 7,792,773 B2 * | 9/2010 | McCord et al. | 706/47 |
| 8,275,110 B2 * | 9/2012 | Vendrow | 379/211.02 |
| 2010/0002865 A1 * | 1/2010 | Kennedy et al. | 379/265.11 |
| 2012/0020471 A1 * | 1/2012 | Erhart et al. | 379/265.1 |

* cited by examiner

*Primary Examiner* — Thjuan K Addy

(57) ABSTRACT

A system comprises a connection accessible to one or more incoming nodes, a call transfer interface for connecting the connection with the incoming nodes to a call transfer module capable of communicating with the incoming nodes, a distributed network of two or more provider nodes interfacing with the call transfer module through a router, the router connected to the call transfer module and provider nodes connected to the distributed network, said provider nodes connected to the incoming nodes through the router connected to the call transfer module connected to the call transfer interface and routed by the router in accordance with a provider node priority.

19 Claims, 16 Drawing Sheets

AUTOMATIC COMMUNICATIONS FORWARDING TO DISPLACED EMPLOYEES

CROSS-REFERENCE TO RELATED APPLICATIONS

This application claims the benefit of prior filed U.S. Provisional Application Ser. No. 61/431,157, filed on Jan. 10, 2011, incorporated herein by reference.

BACKGROUND OF THE INVENTION

The present invention generally relates to a system that assists organizations in the maintaining essential services during periods of crisis by routing incoming communications efficiently.

The operation of critical world economic systems are at risk of disruption by events that interfere with the ability of organizations to continue operations during these events. Events such as natural disasters, disease outbreaks, and acts of terrorism or war can lead to societal upheaval that results in substantial absenteeism among the employees of critical systems. Employees may be unable to travel to their place of employment due to their own unavailability, illness or injury to family members, fear, or directives of governmental institutions. As a result of employee absence at their normal place of business, the continued functioning of necessary infrastructure may be at risk, as well as the disruption of the business operations of even non-critical services organizations.

The organizations that are threatened by chaos arising from disaster are diverse, and range in size from very small to the largest organizations. Examples of small organizations at risk include institutions such as local utilities, local governmental institutions, public safety organizations, and food and fuel wholesalers, distributors and retailers. Larger entities at risk include regional utilities, transportation providers, such as airlines and transit authorities, and governmental organizations such as FEMA and the military.

In many institutions, there is no absolute requirement for all employees to be present at a single, or even normally assigned, place of business. The organization may continue to operate so long as employees maintain access to the company's communications or control systems for normal business operation. There is a continuing need for a variety of institutions to maintain a cohesive chain of responsibility for continuing operations during periods of crisis.

As an example, natural disasters such as hurricanes, wildfires or earthquakes may make travel to the normal place of employment virtually impossible for certain key employees. Thus, those physically inaccessible employees, though otherwise able to carry out their job duties, are absent from their jobs. When absenteeism for organizations such as electric utilities, government agencies, and transportation systems reaches a certain level, their operations cease to function effectively. For instance, following a severe winter storm, travel via public roads may be impossible, leading to excessive absenteeism among customer service representatives of an electric utility. As a result, customers may be unable to contact the electric utility for instructions, or to provide reports of emergencies or power outages. Nonetheless, the customer service agents, though not at their normal (now inaccessible) job locations, could carry out their duties if a functioning communications system were operating.

In a second illustrative example, during the occurrence of a disease pandemic such as an influenza pandemic (or related panic response), absenteeism may reach critical levels across a variety of industries due to illness of employees, illness among employee families, fear of contagion, quarantine, or declaration of a public health emergency. Such absent employees, though unable to travel to their normal job location, may be able to complete their job responsibilities even at a reduced level of efficiency. Presently, there is no available system that in times of crisis can effectively assess employees' location and availability, and then direct communications and operational control to available employees in order to allow continued operation when absenteeism is severe.

A startling example of communications failure leading to a failure of critical economic systems occurred in the aftermath of Hurricane Katrina along the Gulf coast of the United States in September 2004. It is well known that in the days following the hurricane, flooding in New Orleans displaced employees of law enforcement and utility companies, who were unable to effectively communicate with survivors. As a result additional death and destruction of property occurred. In addition, in rural areas of Mississippi not directly affected by flooding, loss of electric power and communications failures led to severe disruption of water, food and fuel supply. If employees of these critical systems had been able to carry out their job responsibilities at remote locations, such disruptions may have been effectively moderated.

In light of the substantial risk of societal disruption and loss of business activity due to severe hazardous events, there exists an acute need for a system and method that provide for a resilient and efficient routing of communications traffic from unavailable representatives of organizations to those agents or representatives capable of performing essential tasks necessary for the continued functioning of the organization.

BRIEF DESCRIPTION OF THE DRAWINGS

For a fuller understanding of the nature and advantages of the present invention, reference should be had to the following detailed description taken in connection with the accompanying drawings, in which.

DETAILED DESCRIPTION OF THE INVENTION

Figure 1:
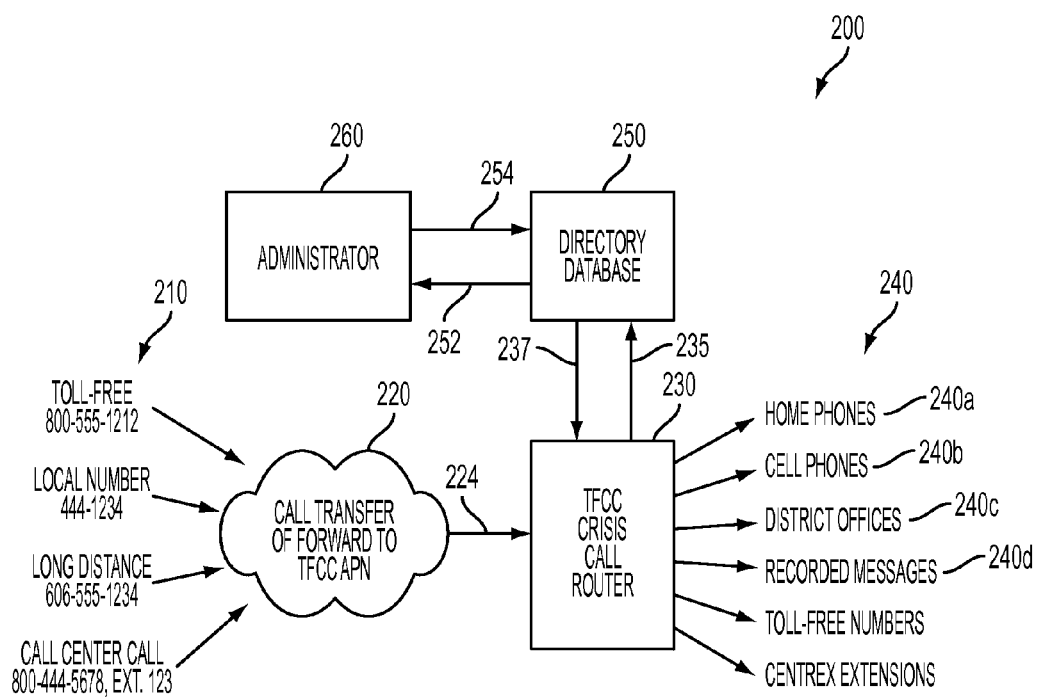
FIG. 1 shows an overview of the crisis telecommunications routing system.

Disclosed herein is a new system and method for providing automatic telephone call forwarding in response to displacement or absenteeism of employees. Clients/users of the system are service providers for one or more aspects of the client user organization. The client utilizing the system redirects their existing or newly created telephone numbers to a connection with the automated call forwarding system described herein. By entering information into the administrative controls of the automated call forwarding system, the service provider clients are able to redirect incoming call traffic to alternative contacts, such as home telephones, office extensions, or voicemail. The system is embodied in a method for distributing a variety of incoming or intra-organizational telecommunications contacts to agents of the organization identified as most capable of efficiently replacing absent or displaced agents. The automatic forwarding of telecommunications contacts operates during periods of telecommunications or societal disruption through a system for redirecting and redistributing incoming telecommunications messages to a communications network according to a user-configurable responsibility arrangement, or a redistribution algorithm. The redistribution algorithm utilizes data from a directory database created at the direction of an organization (service provider), with the directory database being populated with a threaded telecommunications "switching tree." The threaded switching tree provides the information that allows a call routing system to navigate through a hierarchical list of prioritized call destinations to determine service agent availability and predict which available service agents are best suited for providing the services needed by the incoming contact.

The system allows for a client service provider to rapidly update call routing protocols and interactive voice response menus. Administrators of the system for client providers can access the system through a variety of connections, whether over a web connection, or via telephone. A critical capability of the system is to maintain organizational operations of a service provider by ensuring that the supply and service chains are not broken. The supply and service chains may be broken after disruption of communications by the inability of critical service provider agents to operate due to the inability of agents to be present at their normal point of operations. For instance, a pandemic or natural disaster may lead to substantial absenteeism. If the level of absenteeism reaches a high enough level, company operations as a whole may fail because a particular sub-operation is not functioning. In essence the supply and service chains of operation are broken and a company may cease to function if a necessary link in the chains is broken without provision for reestablishment of organizational direction, communication, and control. If a natural disaster leads to excessive absenteeism in the customer service department of an electric utility, for a time, the essential function of the electric utility company (electricity generation and transmission) may continue. If however, absenteeism affects a particular service that is critical to the essential function (I.e. generator operations) without provisions for a back up, business operations may cease, disrupting client activities, and reducing revenue.

The system hosts and accesses an individualized provider directory database. A crisis call routing administrator enters a series of hierarchical contacts into the provider directory database. The hierarchical contacts are service provider agent contacts, such as telephone numbers, extensions, and email addresses to which communications may need to be forwarded. For each department of concern within an organization, one or more contacts are established for replacing supervisory personnel, with the replacement supervisors either being identified from within a particular department or crossing over from related departments to replace needed capabilities. In response to a crisis or to changing conditions during a crisis, a service provider administrator may alter or update a crisis call routing threaded switching tree, whether through a web interface, FTP, or by telephone based IVR. Essentially, the threaded switching tree may be updated by a supervisor or administrator by noting "attendance" or the daily availability of individual contacts, or on a continuing basis. Administrators with sufficient permission level can add, modify or delete records in the directory database. The operation of the crisis communications routing system initiates the generation of a call data record (CDR) for switched communications, with the CDR being useful for monitoring the operation of the system, including wait times, call duration and dropped connections.

The directory database is accessible to a crisis communications router. Incoming telephone calls (or other telecommunications contacts) represent incoming nodes on the distributed communications network, and a communications network connection is accessible to the incoming telecommunications nodes. A call transfer interface is provided for connecting the network connection of various incoming telecommunications nodes to a call transfer module capable of communicating with the incoming telecommunications nodes. The call transfer module is similarly connected to a crisis communications router that routes incoming calls (I.e. incoming telecommunications contacts) to selected service provider nodes (I.e. service agent contacts) according to an algorithm in accordance with a provider node priority determined by reference to the threaded telecommunications switching tree present in the provider directory database. Thus, incoming calls connect to the call transfer interface, connecting to the call transfer module, with the incoming calls then switched by the crisis communications router to connect those incoming calls with available service provider agents. Furthermore, in a preferred embodiment, the telecommunications routing system is configured as a distributed telecommunications network with two or more independently functioning systems available so that in the event that one system fails, one or more additional mirrored systems are available to maintain function of the call routing system. The distributed communications network thus provides multiple service provider nodes interfacing with the call transfer module through a crisis communications router. An incoming telecommunication contact from an incoming telecommunication node is connected to an available provider service agent available at a given provider node after the algorithm of the crisis call router determines that a provider agent is predicted to be available at the given provider node in accordance with the provider node priority of the threaded telecommunications switching tree.

The primary goal of the system is to allow the company to continue essential operations, even if attendance at the normal workplace is impractical. In order to continue operations, the company will seek to maintain direction, communications, and control of operations. For the most effective operation of the new system, a hierarchical directive system should be formulated prior to the activation of the dispersed communication and control system. In a hierarchical system, much as used by military organizations for centuries, direction of operations (I.e. command) is established so that if higher ranked agents are unable to function in their assigned tasks, an agent of inferior rank is identified to step into the vacant positions and complete the job duties of the disabled agent. Thus, as part of its preparedness planning, a company establishes hierarchical responsibility criteria for the operation of individual departments of company operations. For example, an electric utility may be organized into an administrative supervisory department with five administrative agents; a customer service department with one supervisor and 20 customer service agents; a production department with 5 foreman and 50 laborers; and a maintenance department with 3 supervisor agents and 30 repair agents. The agents of different departments may or may not be capable of performing tasks in related departments. Moreover, if no supervisors are available, lower "ranked" agents may be capable, to varying degrees, of undertaking supervisory responsibilities. Identification of a preferred routing of communications and routing of incoming communications to the preferred destination can readily be accomplished by the disclosed system. A number of suggested procedures for engaging in advanced planning for disruptive events are available. See for instance, "National Strategy for Pandemic Influenza," Homeland Security Council, November 2005; "Pandemic Influenza, Best Practices and Model Protocols," U.S. Dept. of Homeland Security, April 2007; "Workplace Preparedness and Response for Disaster and Terrorism," Center for Study of Traumatic Stress, Uniformed Services University School of Medicine; WHO Outbreak Communications guidelines.

Thus, the system is embodied in a method of maintaining critical services by providing for a distributed communications system. The system is further embodied in a method for providing operational redundancy through preparation of machine readable switching directories that utilize identification of agent capabilities, e.g., skill sets, in order to direct communications to agents capable of maintaining a chain of responsibility useful for maintenance of company operations.

A number of systems exist for providing crisis communications on behalf of a number of governmental and non-governmental entities such as police departments and utilities (i.e. agencies). A preferred embodiment of the disclosed system is that incoming telephone calls to a provider are redirected to one or more of a single telephone number (i.e. a VOIP address), up to five prioritized telephone numbers, or sequentially to a series of authority coded contacts, including email. Furthermore, an updateable interactive voice response system (IVR) is provided over a distributed, redundant network to allow customer calls to be routed according to customer responses to the IVR prompts and the redirection protocol, or alternatively to leave an electronic message that itself can be forwarded. Yet another embodiment is a user-selectable voicemail system that overlays a basic IVR coded voicemail system with a system that allows multiple provider agents access to the voicemail system so that displaced provider agents can respond to customer messages as the agents are able, whether through a secondary telecommunications connection, or when certain agents can return to their normal place of employment. Moreover, unroutable telecommunications traffic can be captured by the system to either log the incoming (failed) communications for response or analysis, or to deliver said traffic to a default voicemail box for retrieval as practicable.

The presently disclosed Crisis Call Routing (CCR) system functions as a modular distributed communications network (DCN). Each employee functions as a node of the DCN. Communications routing to and from nodes on the DCN is directed by the CCR system. FIG. 1 shows an overview of the CCR system. The CCR system 200 is formulated to, when activated, accept incoming communications from a number of sources 210. Incoming sources 210 are typically telephonic communications links, for instance, utility toll free numbers, local telephone contacts, long distance telephone calls, voice over internet (VOIP) calls, or redirected calls from a call center. Those skilled in the art of telecommunications recognize that incoming communications may arrive from a variety of additional sources, such as SMS text messages, email messages, facsimile transmissions, satellite telephone and radio telephone communications. The wide variety of sources of origination of incoming calls or other client contacts each represent an incoming telecommunication node, wherein each incoming telecommunication node is a contact to the CCR system which will if possible be routed to the appropriate destination. All incoming telecommunications contacts might not originate from outside a particular organization; on the contrary, the system is adaptable to effect the appropriate routing of intra-organizational call traffic. Incoming contacts (I.e. calls) are contacts that originate outside, or "upstream" of the CCR system.

The system as presently embodied is adaptable for providing communications between a wide variety of telecommunications sources. Call transfer module 220 accepts incoming communications from a given node, and modulates those incoming communications to a uniform protocol, as shown at arrow 224, connecting the incoming communications to the CCR system router 230. Router 230 will then direct, i.e. switch, the incoming communication to a designated destination, 240a-240d. The designated destinations such as 240a-240d represent contact points for agents of the service provider being contacted by the client initiating the incoming communication. The points of contact between the system and the service provider agents are considered service provider nodes. Passage through the call transfer module 220 and the CCR system router 230 produces a telecommunications signal that is compatible (and/or transferable) to the designated destinations at the service provider nodes 240.

Directory database 250 is a database which provides a hierarchical listing of agent contacts (service provider nodes). The hierarchical contact listing is entered to prioritize the destination of incoming communications to those provider agents most capable of providing the service requested in the incoming communication. Directory 250 is arranged to provide a variety of fields, including, for instance, a hierarchy of projected communication destinations (e.g. telephone numbers) for personnel, and personal attribute designations which identify the operational capabilities of various personnel who may be capable of assuming responsibility when an agent higher in the operational chain of responsibility is unavailable.

To operate the CCR system, a client provides information to populate the fields of directory database 250. Typically the directory database is populated via an internet web interface, file transfer protocol, or an update merge protocol. The directory database is updateable when the CCR system is operable through batch filed transfer on a near real-time basis. Once the directory database is in place, the system is activatable by a provider agent administrator or an administrator of the CCR system, optionally provided that an authentication protocol is successfully completed. Upon activation, incoming sources 210 are directed to the call transfer module 220 from where communications traffic is redirected to those destinations designated via the CCR system router 230. As will be described below provider agents can update directory 250 to provide their preferred telecommunications connection node. When forced by circumstances to work away from their normal work location, incoming communications are thus either directed to that agent's alternative telecommunication destination node, or to an alternative agent with identified capabilities for providing the service desired by the incoming caller.

Through means of the call transfer interface that is part of call transfer module 220, the system allows interoperability between a variety of telecommunications systems, incompatible carriers and telephonic protocols. Thus incoming calls from a "Sprint" network may be transferred to an otherwise incompatible "AT&T" network, a toll call to a toll free number, or a toll free number to a local number. Furthermore, incoming contacts are modulated by call transfer module 220 in order to operate through a variety of connections, whether internal telephone connections, Centrex or PBX based systems, or from toll free numbers.

Clients participating in the CCR system will provide interconnection information necessary to redirect incoming telecommunications (e.g., toll free or local calls to the client) to a connection with the call transfer module 220. The system functions under the presumption that a client is able to initiate redirection of incoming telecommunications to the system. The directory database for a particular client is provided with the contact node information necessary in order to redirect incoming telecommunications traffic to alternative locations 240, such as a provider agent's residential telephone, cellular telephone, or the like. The CCR router 230 communicates, as shown via arrow 235, to query directory database 250 for the proper alternative location to which to forward the incoming telecommunications traffic, in accordance with the hierarchical system constructed via the administrator interface 260 (via arrows 252, 254).

In a preferred embodiment of the system client service providers redirect incoming telephonic communications traffic to the CCR system, which then redirects the incoming call to another (one or more) toll or toll-free telephone numbers, such as a residential telephone. Calls can alternatively be redirected to up to five alternative telephone numbers with calls directed to multiple telephones based on the routing algorithm. The number of redirects may be unlimited, however it is preferred that this number be limited as described to reduce system complexity and database loads. Redirection may include, for instance, sequential ringing of multiple telephones with roll over ringing to the next priority telephone on an unsuccessful connection. In another preferred embodiment, accessing an active voicemail or answering machine is considered a successful call. The CCR system provides an updateable IVR system, providing a courtesy response message that answers all incoming telephone calls with a broadcast message if no alternative routing is available, with a disconnection following the broadcast message. The system may be configured with a static IVR call routing program that prompts callers to provide information necessary for the proper routing of their call, such as entry of a desired extension number. In a further embodiment, a default voicemail option is available either automatically on initiation of the CCR system or if no other higher priority telephone contacts are available, with the voice mail system allowing access to temporarily absent service agents at their convenience. The voicemails left as a result of incoming calls can be optionally delivered to designated service agents via email, over the internet, or telephonically. A further embodiment is an option for service providers to schedule the initiation and or termination of routing features and particular routing threads, or for the initiation and termination of the operation of call forwarding to be manually controlled.

Figure 2A:
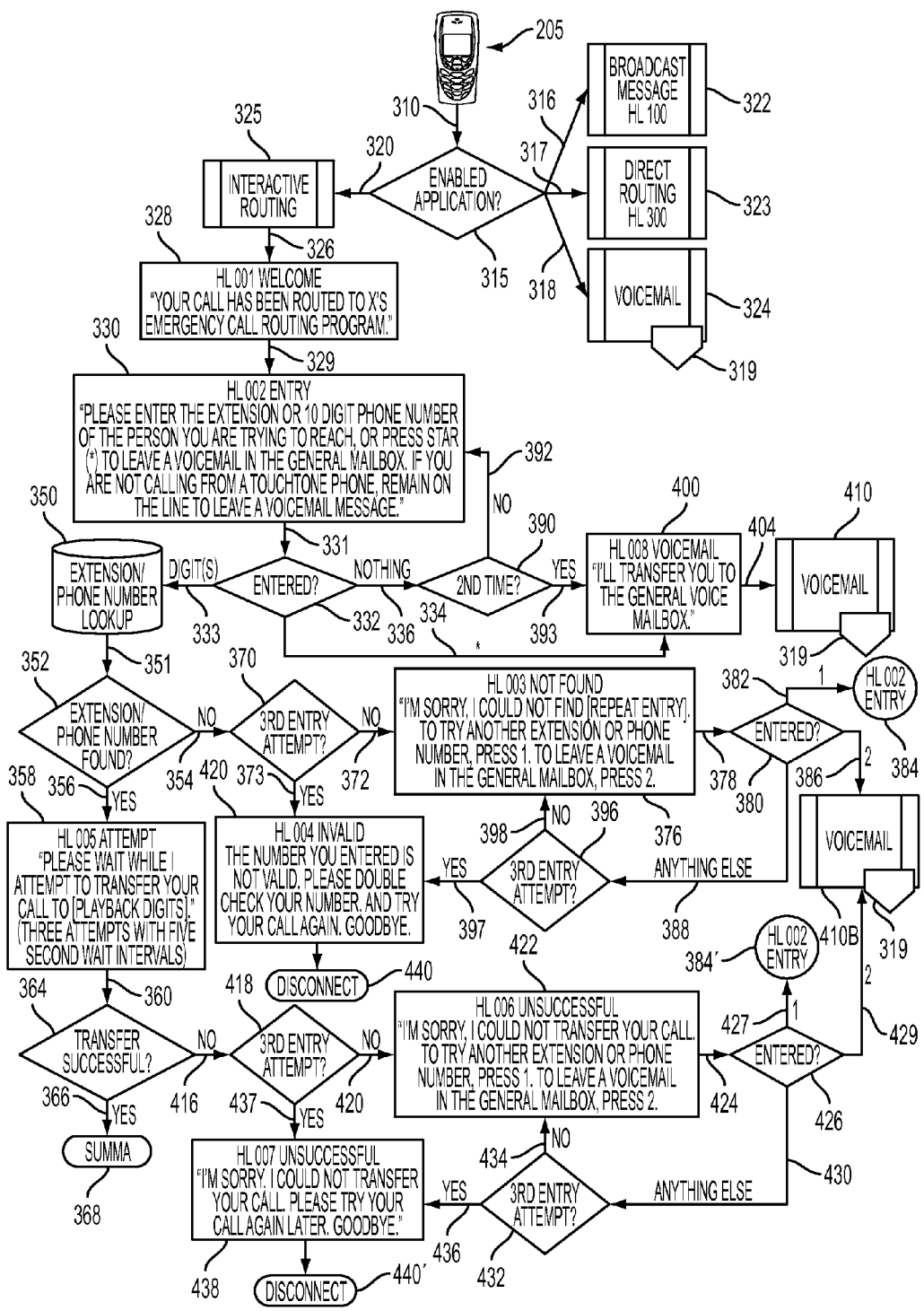
FIG. 2A-B shows a call flow diagram of an incoming telecommunications call.
Figure 3A:
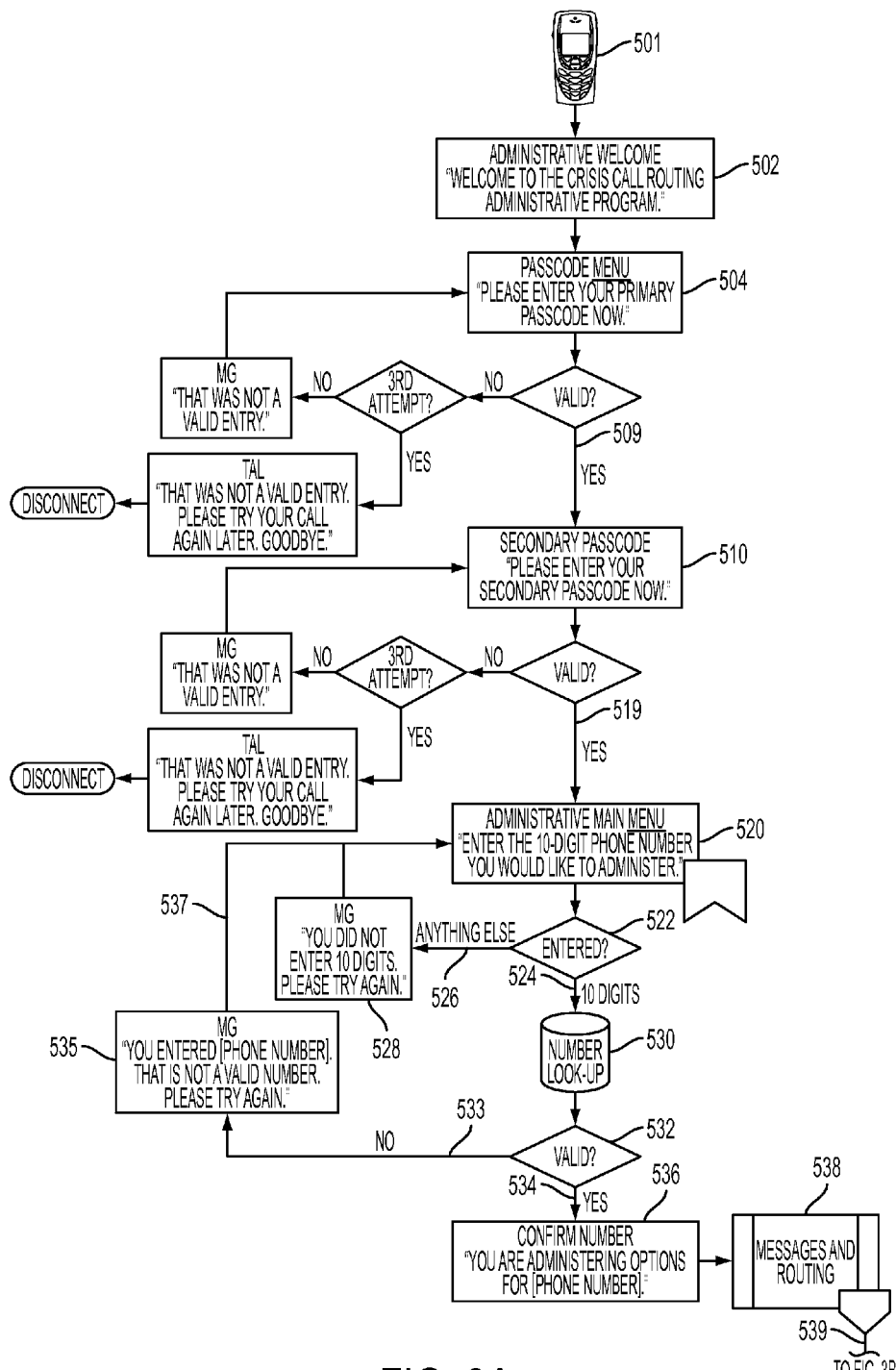
FIG. 3A-H shows the administration of the directory database.
Figures 1, 3B:
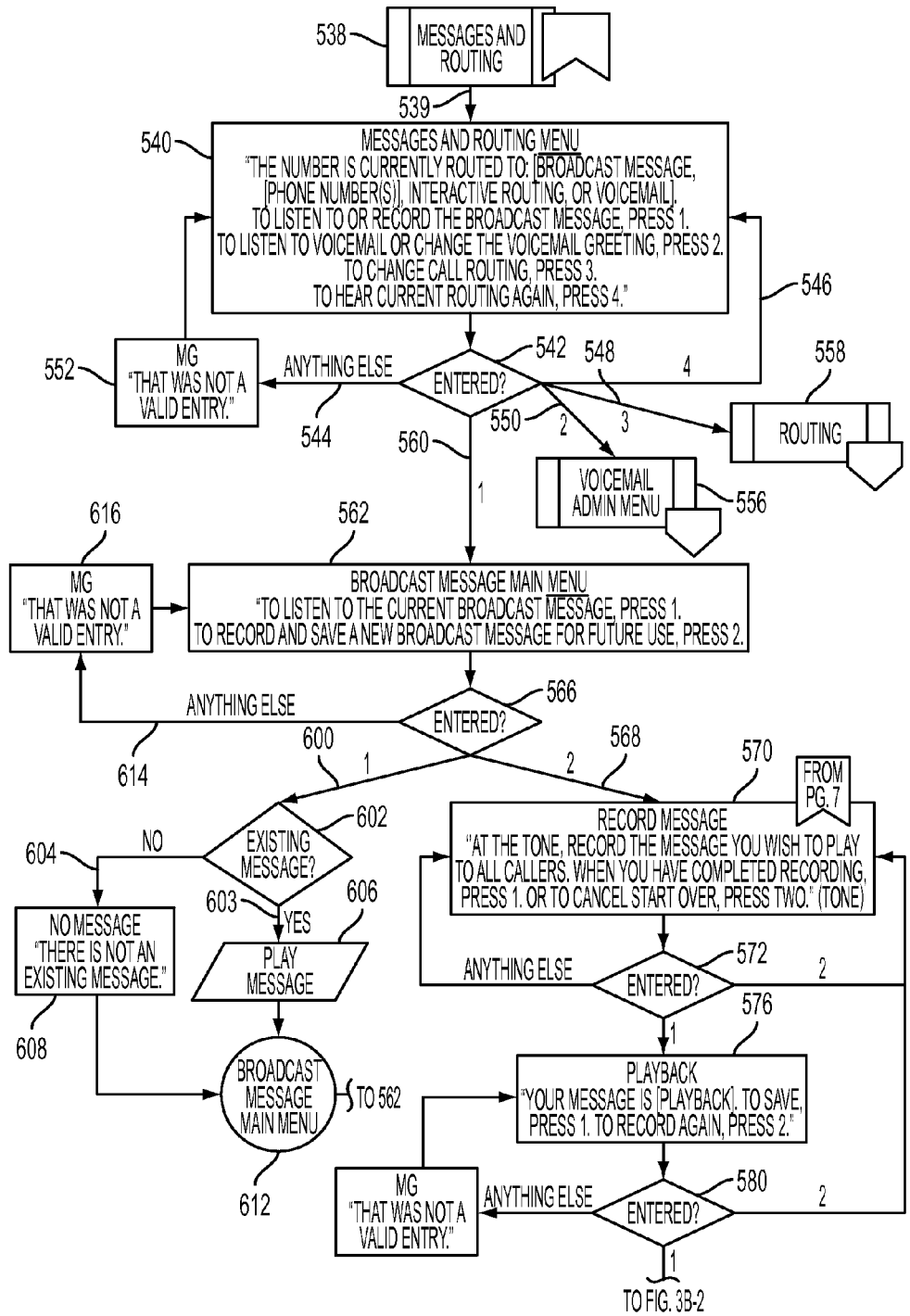
Figures 2, 3B:
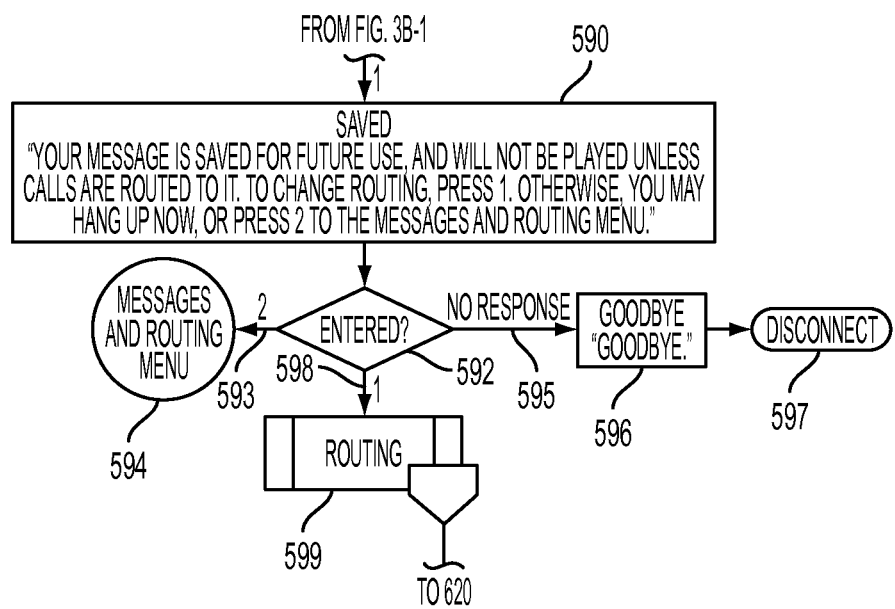

Turning now to FIG. 2, a call flow diagram of an incoming telecommunications call is shown. In FIG. 2A, incoming call 205 is directed to one of the telecommunications connections of the provider (company utilizing the CCR service). The redirection of telecommunications to the CCR system is preferably initiated by action of the provider, by forwarding calls to open nodes on call routing service call transfer application 220, described in relation to FIG. 1. When the call transfer protocol at 220 is invoked, incoming calls are transferred to a connection with the CCR router 230. It should be noted that the forwarding of incoming calls to nodes of the call routing service can be embodied as a separate action on the part of the provider from the enabling of the CCR routing system. In a preferred embodiment, the call transfer function is linked to the CCR routing system, wherein activation of the CCR routing system is necessary to initiate transfer of incoming calls from a provider contact number to nodes of the call transfer application 220.

As shown at box 315, the connection of an incoming call 205 interacts with the CCR system controller, as at arrow 310, and an initial query is presented as to whether the CCR interactive routing module 325 has been set to the active state. If module 325 has been activated, then as at arrow 320, a connection is made between the incoming call 205 and the interactive routing module 325. The status of interactive routing module 325 and the call redirecting pathway of incoming calls are typically enabled and disabled by means of a telephone connection between the system and an authorized system administrator, or alternatively via a web interface available to authorized administrators, or scripts delivered by email, text message or the like.

If the interactive routing module has not been activated, one or more alternative call transfers may be optionally provided, such as at arrow 316 leading to box 322, delivery to the incoming call connection a general broadcast message (i.e. HL 100) providing general status or emergency information. An example of a general status broadcast message would be "We are sorry, but due to the disaster, we are unable to provide service at this time. If there is a life threatening situation, please call 911, or contact law enforcement that are present at the scene." Alternatively, as at arrow 317 leading to box 323, the incoming call can be directly and or automatically routed to one or more predetermined alternative telephone numbers (or contact nodes). In a preferred embodiment, when the interactive routing module is inactive or otherwise unavailable, the incoming telephone call can be routed to 5 or more sequentially alternative telephone contact numbers, possibly provided to the system prior to the occurrence of a crisis. A further alternative, as shown at arrow 318 leading to box 324, is that incoming calls are delivered to a general voicemail system, with a telephonic greeting recorded previously in an administrator program or up-loaded by a qualified system administrator. The operation of the voice mail system during crisis situations is FIG. 2B, following arrow 319.

The interactive routing module 230 is shown schematically in FIG. 2A as box 325. When interactive routing module 325 is active and available, arrow 326 leads to initiation of an announcement at box 328. An entry HL 001 may provide a welcome to the CCR routing system, announcing for instance: "Your call has been routed to your provider's emergency call routing program. Please stand by to assist us in properly routing your call." Following arrow 329 to box 330, instructions are provided to the caller as entry HL 002, and may state, for instance "Please enter the extension of the person you are trying to reach, or press star (*) to leave a voicemail in the company's general mailbox. If you are not calling from a touchtone telephone, please stay on the line to leave a voice mail message." In response to the query presented at box 330, at box 332, the responses to the query presented by HL 002 are integrated, depending on what is entered following the query 330. If a (*) is entered, then arrow 334 is followed, connecting the call to a voice mail system, whether that of the provider's system (if such system is extant and operable) or to a voice mail system that is part of the CCR system. As at box 400 a voicemail announcement, entered as HL 008, may announce, for instance, "I'll transfer you to the general voice mailbox." Arrow 404 shows the connection of calls connecting to the general voice mailbox at box 410. As shown at arrow 336, if no entry is detected, the system is configurable at box 390 to repeat the initial announcement, following arrow 392 to box 330, where announcement script HL002 is provided. A second alternative announcement may be made to the caller (not shown in FIG. 2A), or a transfer is made to the voicemail system via arrow 393 to announcement 400.

Interactive routing module 325 is configured to detect the entry (e.g., via a keypad, or by pulses, tones, or voice) of digits representing a telephone number or internal extension number. If such digits are entered, following arrow 338 leads to a query being presented to the directory database system 350 in order to identify the status of the extension and or telephone number. The system is preferably configured to detect up to the first ten digits entered, or alternatively to detect four digits, fourteen digits, or to announce an error message if an unexpected number of digits are entered. Responses from the directory database query include such options as "no such extension," "number not available," (for instance due to a system fault), "extension found and available, no transfer indicated," and "number found and available, second transfer indicated." The operation of directory database system 350 is described in greater detail in the discourse that follows. Arrow 351 leads to the directory database response to the extension status query at box 352. FIG. 2A does not provide an exhaustive description of all possible redirection of incoming calls, but is provided to illustrate the manner in which the directory database can be configured in order to effectively channel incoming call traffic during crisis situations in order to enhance the ability of a provider telecommunications system to continue to function during times of stress. If no extension identity is found in the directory database, arrow 354 is followed. If the extension number entered matches an entry in the directory database 350, then arrow 356 is followed to box 358.

Announcement script HL 005 notes the projected ability to successfully transfer the incoming call by announcing, for instance "Please wait while I attempt to transfer your call to (a given extension)." Typically, the system is configured to attempt to connect the incoming call to the requested extension by attempting to connect three times, with a five second wait between attempted connections. It will be apparent that a system administrator is provided with the capability to adjust attempts such as that at box 358 in response to current conditions. For instance, if incoming call volume is low, yet successful connections are infrequent due to damage to or unavailability of extensions, repeated attempts can be reduced because subsequent attempts are not expected to be successful. If incoming call volume is high, and the successful transfer of incoming calls to extensions is limited by excessive volume rather than system malfunction, then additional attempts to successfully attempt connection can be allowed, or the wait interval extended or both. Other alternative attempt parameters may include, for instance, two attempts with a thirty-second wait interval and eight attempts with a three-second wait interval.

Arrow 360 leads to the query of an indication of successful transfer at box 364. If the incoming call is successfully connected to the requested extension (or alternative extensions as provided in directory database 350) arrow 366 is followed. A number of call connections can be created to connect the incoming call with the routed extension. One alternative is for the establishment of a direct connection between the incoming call and the extension to which the call is routed, with the CCR system dropping its connection to the call—an option that may be preferable if CCR system associated resources are needed to effectively continue operation. Alternatively, a SUMMA connection can be created, wherein the incoming call traffic continues to transit through CCR system resources for the duration of the call. Advantages of establishing a SUMMA connection include the ability to monitor call quality and call continuity for quality control purposes; effective logging of call traffic as a service to providers using the CCR system, and the ability to reroute the call connection through a distributed telecommunications network that may, for instance, be experiencing localized stress, disruption, or excessive traffic. A variety of other telecommunications network connections may be enabled, including Excel, TCPIIP, and X.25.

If at box 364 an unsuccessful connection is indicated, arrow 416 leads to box 418, a query as to whether the connection attempt is the final indicated connection attempt as specified by the parameters set at box 358. As shown in FIG. 2A, three attempts are specified. If the result of the query at box 418 is no, another connection attempt can be optionally made, as in boxes 358 and 364. Alternatively, arrow 420 may be followed to box 422 in order to provide the caller of the incoming call the opportunity to alter their connection strategy. At box 422, announcement script HL 006 indicates an unsuccessful connection attempt, and provides alternative paths for connecting the incoming call. For instance, HL 006 may announce "I'm sorry, I could not transfer your call. To try another extension, press 1, to leave a message in the general voicemail box, press 2, otherwise hold the line while we try again." The responses to the query announced at box 422 are integrated by following arrow 424 to box 426. At box 426, the system awaits a response to the query at 422. If the response is an entry of a "1," arrow 427 leads to box 384' and loops back to box 330, where announcement HL 002 invites entry of an extension number. If the response is an entry of "2," arrow 429 is followed to initiate a transfer of the call to the voice mail system 410. If any other entry is made, or no entry is made, as at arrow 430, the configured wait time is allowed to elapse and another attempt to transfer the call is made (by following the process set out in boxes 358, 364 and 368). In the instance that the call transfer is again unsuccessful, the query at box 432 again is made to determine whether the attempt is the final attempt (i.e. third attempt in the given example). If not, arrow 434 optionally leads back to box 422, allowing the caller to choose another extension.

If the response to either query at box 418 or 432-whether the attempt was the final provided attempt—is yes, arrows 436 and 437 lead to box 438. The process of terminating the unsuccessful call is initiated at box 438. Announcement script HL 007 is read to the caller, stating, for example, "I'm sorry, I could not transfer your call. Please try again later. Goodbye." Whereupon the call is disconnected at box 440'.

The "SUMMA 4" protocol is an industry recognized telephone switching protocol available from Cisco Systems. A Summa switch is a programmable switching system that provides an interface between a publicly switched telephone network (PSTN) system (e.g., a public utility such as AT&T or Sprint) and private telecommunications network services. See for instance, U.S. Pat. No. 6,480,597 to Kulp, et al., issued Nov. 12, 2002. One advantage of using a Summa-type switching system is that the hardware handling the CCR router module and related components functions independently of network-specific or vendor-specific telecommunications services, allowing the routines described herein to function as described regardless of the particular network that is originating the incoming call and the telecommunications network to which the routed call is delivered.

Figure 2B:
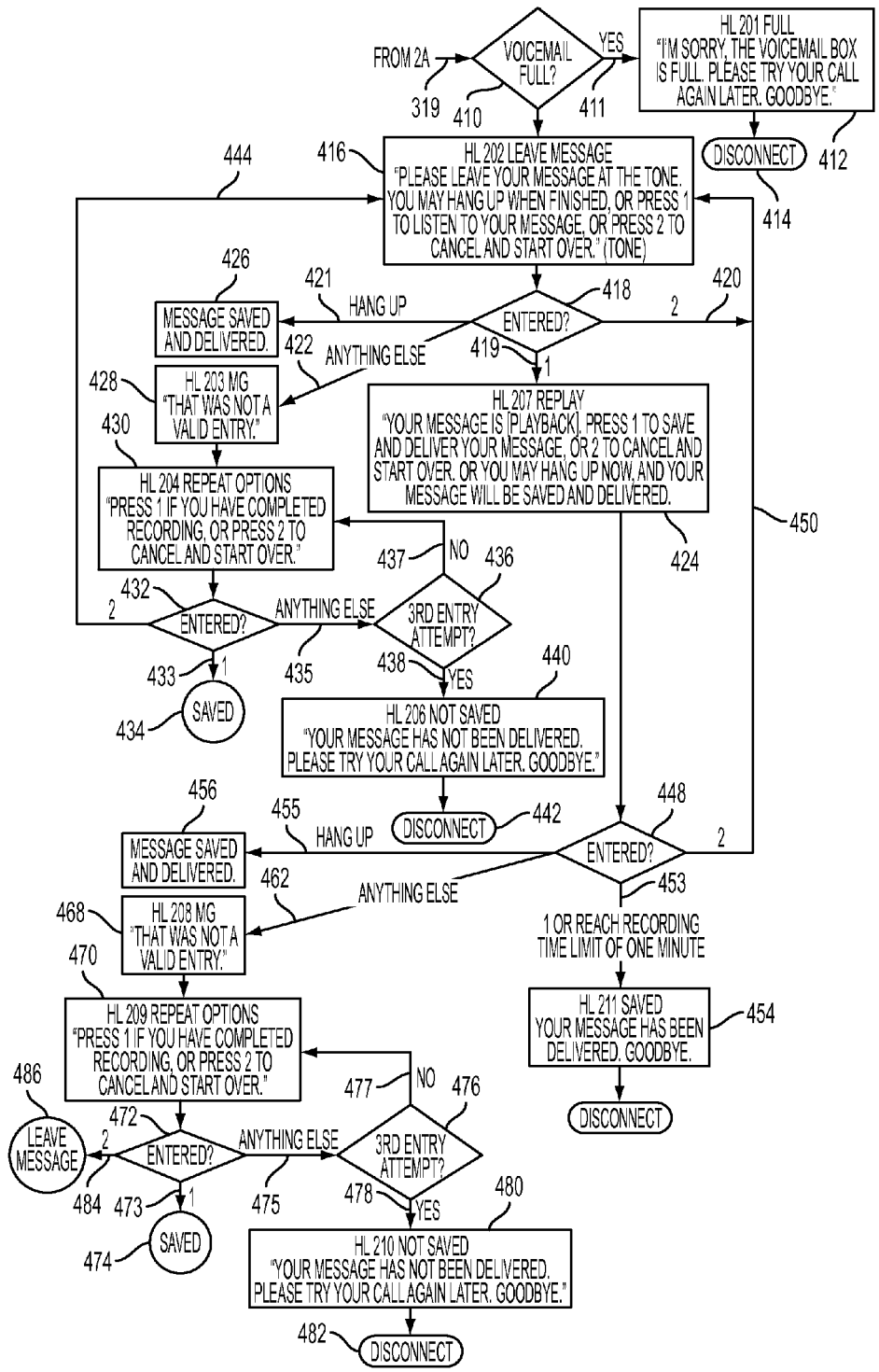

Returning now to the voicemail application, following arrow 319 to FIG. 2B leads to the query at box 410 as to whether the routed voice mail system is full. If the mailbox is full, as at arrow 411, announcement HL201 informs the caller of said condition at box 412, announcing, for example, "I'm sorry the voicemail box is full. Please try again later." The call is then disconnected at box 414. If as at arrow 415, the voicemail box is not full, announcement HL202 instructs the caller about options for leaving a message at box 416, announcing, for example, "Please leave your message at the tone. When you are finished you may hang up, or press 1 to review your message, or press 2 to cancel your message and try again," whereupon a tone is delivered. In response, the system queries whether a digit is keyed into the telephone. If a "2" is entered, arrow 420 is followed to return to box 416, allowing reentry of a message. If a "1" is entered, the recorded message is replayed and HL 207 is announced, for instance, press 1 to save your message or 2 to cancel and start over, or you may hang up and your message will be delivered."

If at box 418, a hang up condition is detected as at arrow 421, the message is saved and delivered to the appropriate provider agent nodes at box 426. If any entry besides a "1," a "2," or a hang up occurs at box 418, as at arrow 422, at box 428 an announcement states as at HL203 "That was not a valid entry," and at box 430 HL 204 announces the available options once again. In response to the query at box 432, if a "1" is entered, as at arrow 433, the message is saved as at box 434. If a "2" is entered at query 432, then arrow 444 is followed to return to box 416 and a second attempt is made to leave a message. If there are any other entries as at arrow 435, a query at box 436 determines if the unresponsive entry is the third attempt to answer the query at 432. If so, arrow 438 is followed to box 440, wherein an announcement is read indicating that the message has not been saved as HL206, and the call is disconnected at box 442.

Returning to box 424, if the response provided at box 448 is a hang up condition as at arrow 455, the message is saved and delivered to the appropriate provider agent nodes at box 456. If any entry other than a "1," a "2," or a hang up occurs at box 448, as at arrow 462, at box 468 an announcement states as at HL208 "That was not a valid entry," and at box 470 HL 209 announces the available options once again. In response to the query from box 470 at box 472, if a "1" is entered, as at arrow 473, the message is saved as at box 474. If a "2" is entered at query 472, then arrow 484 is followed to box 486, and a second attempt is made to leave a message, as at box 416. If there are any other entries as at arrow 475, a query at box 476 determines if the unresponsive entry is the third attempt to answer the query at 472. If so, arrow 478 is followed to box 480, wherein an announcement is read indicating that the message has not been saved as HL210, and the call is disconnected at box 482.

The operation of the emergency call routing system disclosed herein relies in large part on the effective construction of the directory database and the threaded priority node designation provided therein. The administration of the directory database, as described with respect to box 250 of FIG. 1, is disclosed in additional detail in FIGS. 3A-H. An administrator of the CCR system for service providers or a service provider supervisor or service provider agent contacts the administrative program for the CCR system, either through telephone, via terminal interface, or web/internet interface. As described in FIG. 3A, administrator 501 telephones the administrative telephone interface at box 502. At box 504 the administrator is prompted to enter a passcode. The system as embodied in FIG. 3 utilizes a two level passcode system to provide heightened security. Other enhanced security can similarly be utilized, whether by biometric indicators, IP address based validation, or other available security systems. If a valid primary passcode is entered as at arrow 509, at box 510 the administrator is prompted to enter a secondary passcode. If the appropriate secondary passcode or other security indicator is provided, as at arrow 519, an administrative menu announcement at box 520 prompts the entry of a telephone number (i.e. an incoming telecommunications node) that is to be administered. As shown in FIG. 3A, if entry of a node identifier is entered at box 522 as a 10 digit telephone number, as at arrow 524, the number is looked up in the directory database at box 530. If any entry is made other than a 10 digit number, as at box 526, the administrator is prompted at box 528 to attempt entry once again. In the case that the entry at 522 is not a valid administrable number as at arrow 533, at box 535, the administrator is prompted to attempt entry of a valid number again, returning to box 520 via arrow 537. If the entry at 522 is a valid administrable number as at arrow 534, the administrator is requested at box 536 to reenter the contact number for administration, whereupon box 538 leads through arrow 539 to the message and routing menu at box 540, on FIG. 3B. As shown in FIG. 3, relatively simple administration processes can be carried out telephonically. It is apparent that more complex routing schemes and administration processes are better suited for being set up via a computerized or graphical interface, such as using a networked terminal or laptop computer, or through an internet enabled computer using the world wide web, for instance. Nonetheless, the structure of the administrative system will be functionally equivalent to that disclosed with respect to FIG. 3.

Box 540 provides for four or more administrative menu options. The system first provides an announcement of the current status of the incoming node being administered, indicating for instance the provider node destination of communications directed to the incoming node: a forwarded telephone number, an interactive routing algorithm, or to general voicemail. The administrator is then prompted to choose among several options by entering a menu code, wherein, for instance, entry of a "1" allows administration of the broadcast message options; entry of a "2" allows administration of voice mail options entry of a "3" allows administration of interactive routing options, and entry of a "4" repeats the routing status announcement. Entry of a "4" thus leads through arrow 546, back to the menu at box 540, wherein the status announcement is repeated. Entry of a "3" as at arrow 548 directs the administrative function to open the routing administrative functions as at box 558; entry of a 2 leads through arrow 550 to the voice mail administrative functions at box 556. In this example, if any other (invalid) entry is provided, as at arrow 544, leading to box 552, an announcement indicates the invalidity of the entry and returns the administrator to the menu at box 540.

When entry of a "1" response occurs at box 542, arrow 560 leads to the broadcast message main menu at box 562. The broadcast main menu prompts the administrator with the options to either listen to the broadcast message by entering a "1" or to record and save a replacement message by entering a "2." A response to the query at 562 is entered at box 566. If the response is any response other than a "1" or "2", arrow 614 is followed, whereupon an announcement at box 616 is made indicating that no valid entry was made, and a return to the broadcast message menu occurs again at 562. If the response at box 566 is a "1", then arrow 600 is followed to box 602, whereupon the system determines whether an existing message has already been stored. If the determination is that there exists a message, arrow 603 is followed to box 606, directing the system to play the preexisting message and the stored message is played to the administrator. If no message is presently stored, arrow 604 is followed to box 608, whereupon an announcement is made that there is no existing message. In either case, the administrator is returned to the broadcast message menu 562, at box 612.

If in response to the prompts at box 562, the response entered at box 566 is a "2", then arrow 568 is followed to the message recording protocol. After entering and approving a broadcast message, the message is saved as at box 590, and subsequently the administrator is prompted to enter a either "1" or a '2' if further administration is desired. If no response is detected, arrow 595 is followed and the administrative call is disconnected. If a '2" is entered, arrow 593 is followed, returning the administrator to the messages menu at box 594.

Figure 3C:
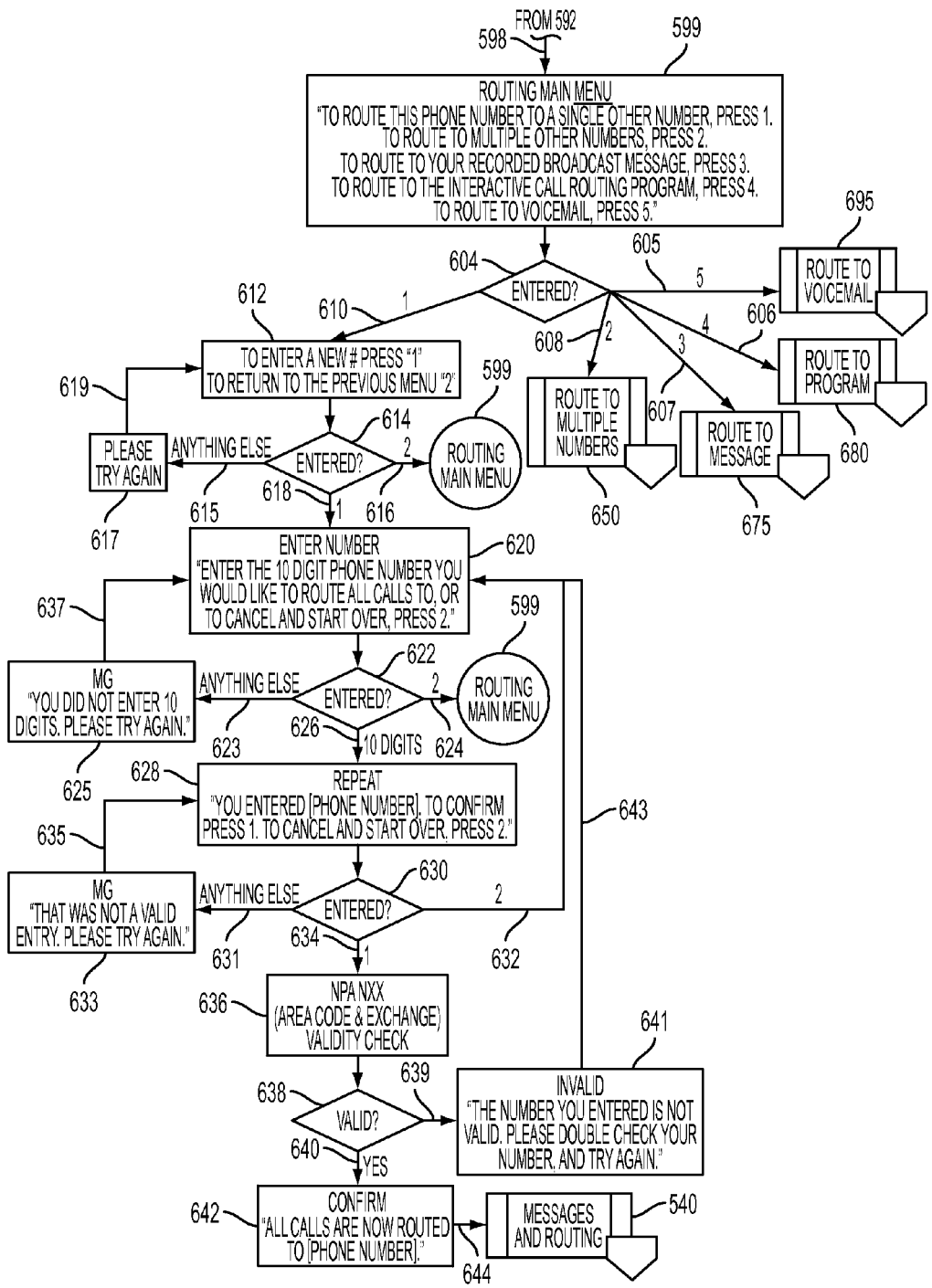

If a "1" is entered at 592 in response to the query at 590, the administrator follows arrow 598 to the routing main menu at box 599. Turning to FIG. 3C the routing main menu allows the administrator to direct communications from the incoming communications node to one or more of: a single contact or telephone number; multiple other numbers based on a call priority algorithm; a broadcast message; an IVR system; or directly to voicemail. For instance, if, in response to the query at box 599, a "1" is entered at box 604, arrow 610 is followed to a protocol for routing to a single contact node beginning at box 612. The number to be routed to is entered at box 622 in response to the query at box 620. If a 10 digit number is entered, arrow 626 is followed and the number is announced at box 628 where the administrator is directed to confirm entry at box 630. If the number is confirmed, arrow 634 is followed and the validity of the entered number is checked by the system at box 636. If the number is valid, arrow 640 is followed to box 642 where the number being routed to is announced yet again. Arrow 644 is then followed, redirecting the administrator to the messages and routing menu at box 540.

Figure 3D:
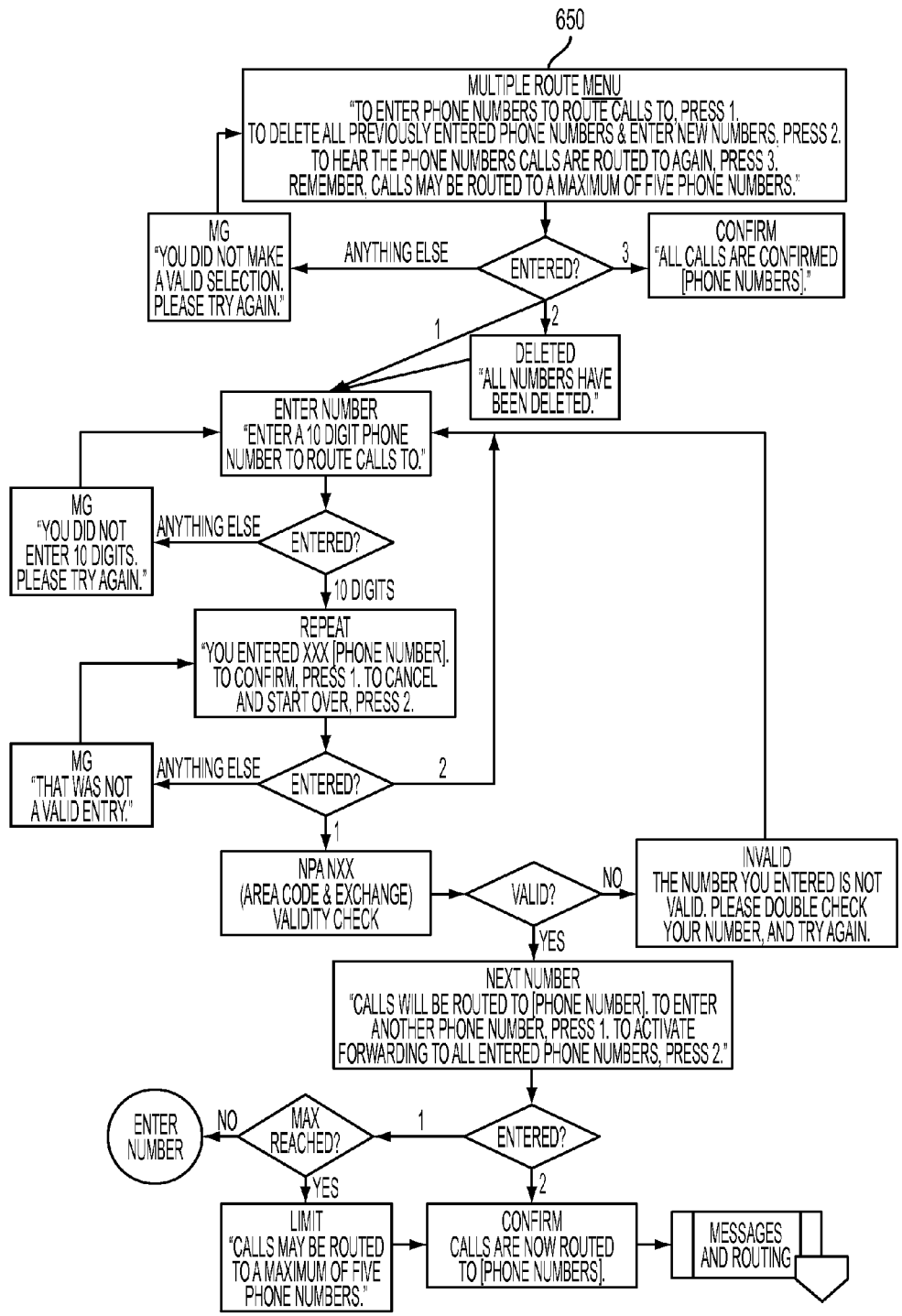
Figure 3E:
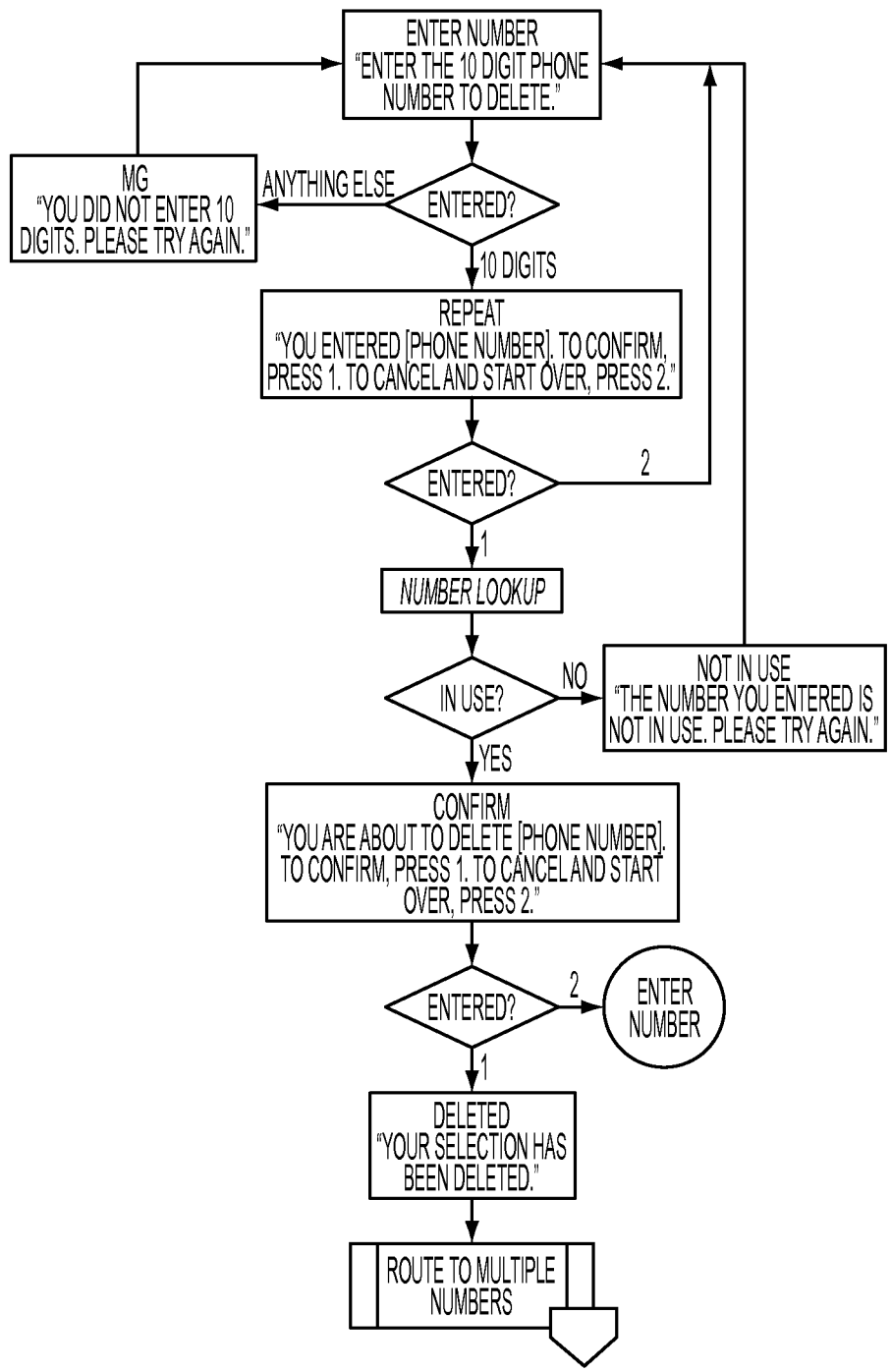
Figure 3F:
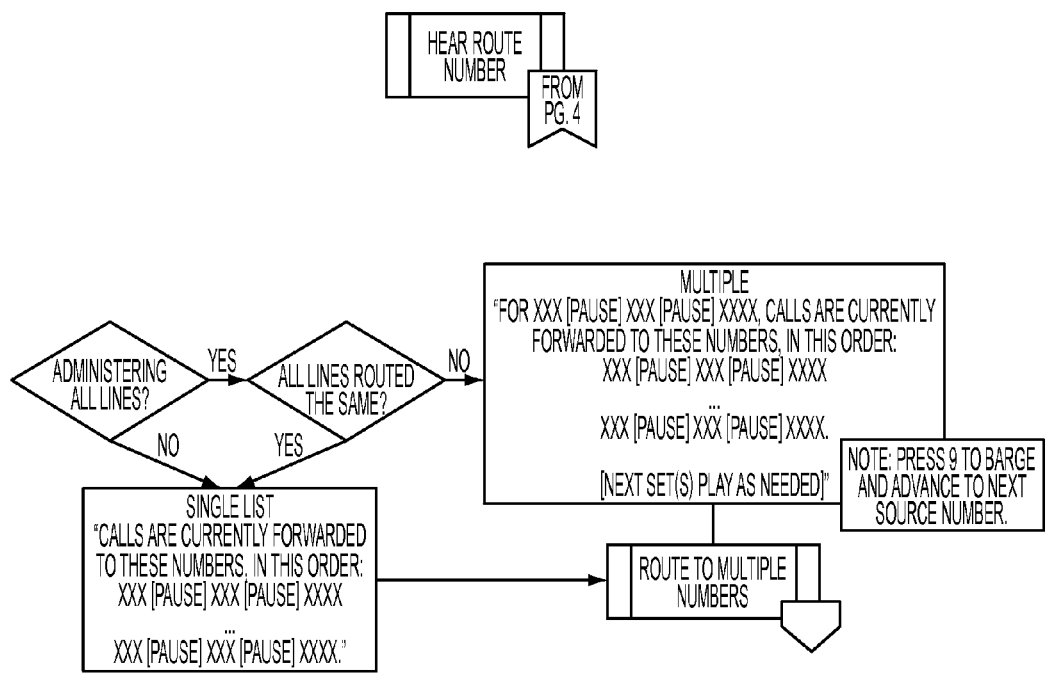
Figure 3G:
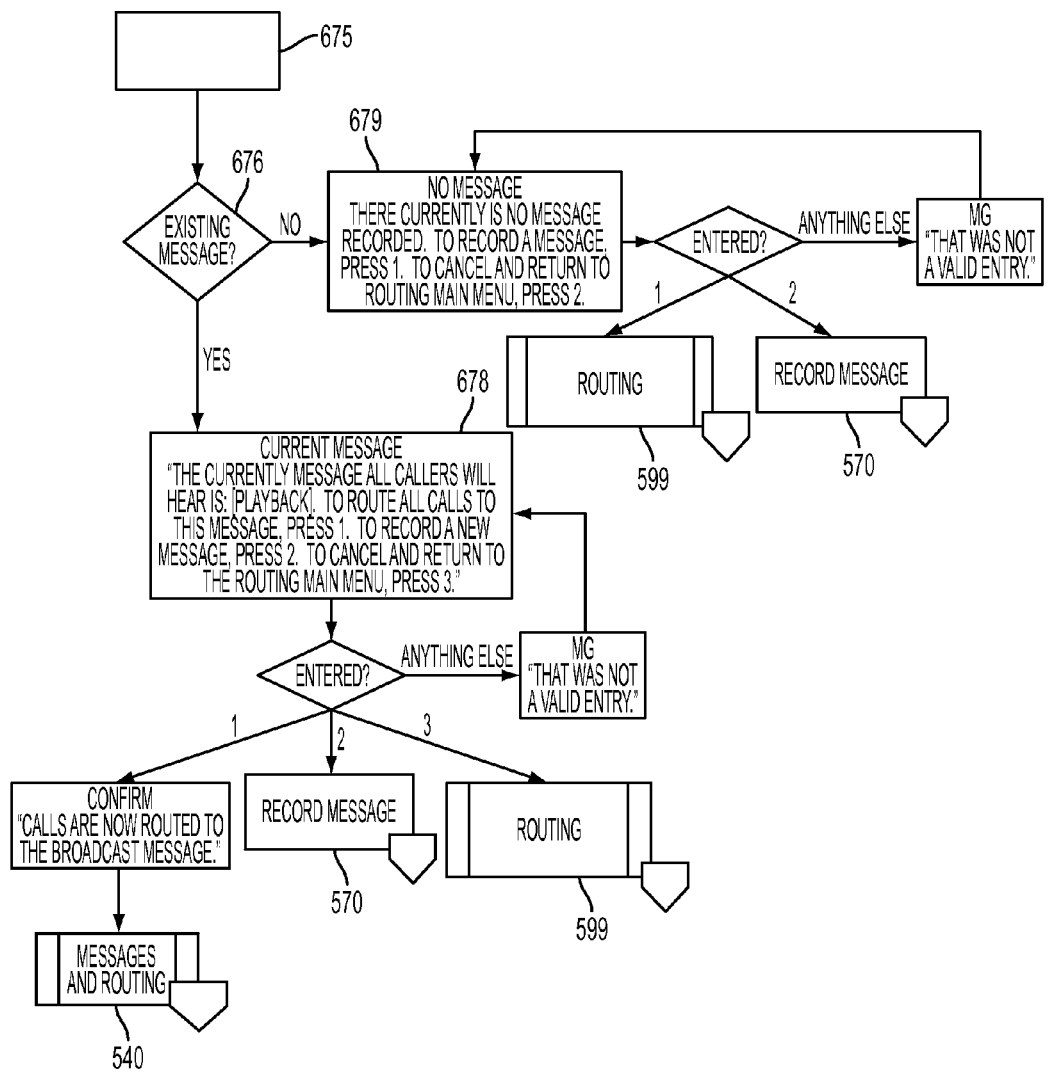
Figure 3H:
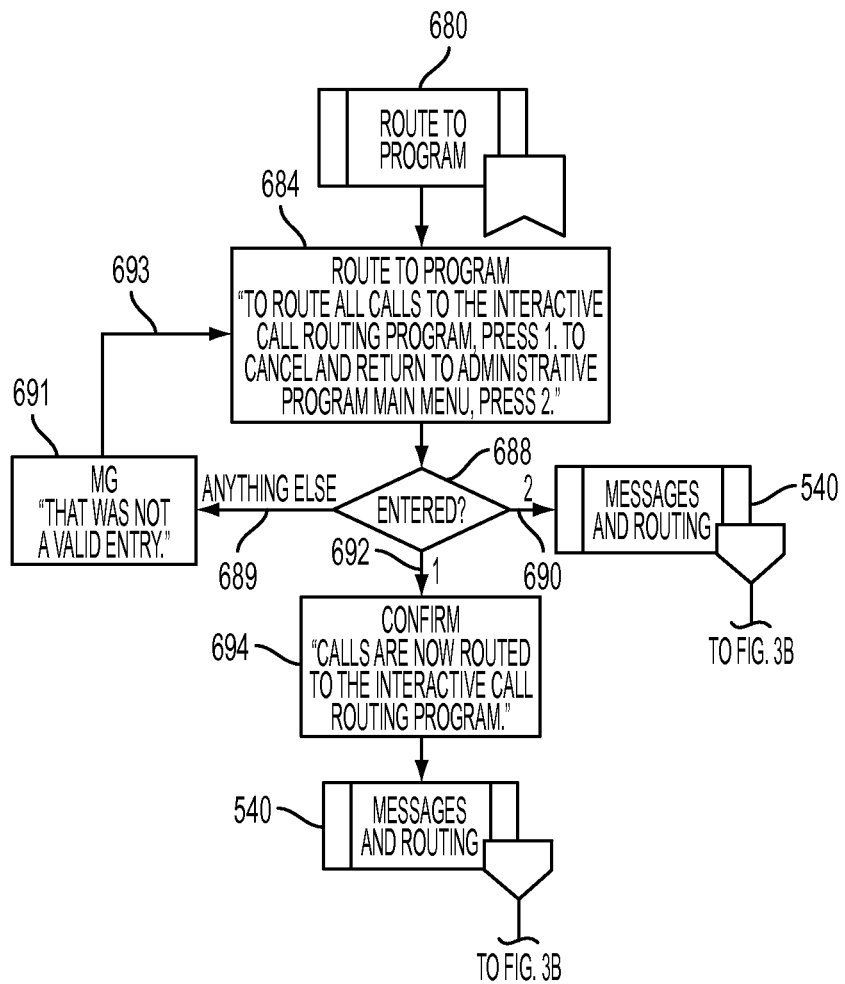

When the response to the query at box 599 is entered 604 is a "2", then arrow 608 is followed to box 650, wherein the administrator may enter multiple other numbers to be routed to, as in FIG. 3D. A response of "3" results in arrow 607 being followed to box 675, wherein the administrator may enter a prerecorded broadcast message to which incoming contacts may be routed, as in FIG. 3G. Alternatively, the administrator may choose to route to a program, at 680 via 606, by entering a "4" and choosing the appropriate interactive program, such as an IVR, as in FIG. 3H.

Incoming telecommunications contacts (incoming contacts) may be in the form of telephone calls, SMS text messages, instant messages, email messages, or other electronically modulated communications. The system is configured to maximize the efficiency of incoming contacts reaching a provider agent capable of performing the actions sought by the incoming contact. Thus, it is preferable that the provider engage in planning prior to the incidence of an event that results in disruption of services. Each provider agent or particular job responsibility is associated with a contact code number, which will typically be in the form of a telephone number or extension, an email address, or an IP address. Each alternative contact code number is equivalent to an incoming contact node, wherein the provider node (a contact node) is the location on the telecommunications network where the provider agent with a particular responsibility is expected to be reached. Thus a particular provider node may be accessible to a number of customer service representatives, e.g., an accounts payable call center with several customer service representatives having access to incoming telecommunications messages through a single contact node. Conversely a single provider agent may be accessible through a number of provider nodes, for instance company land-line, company cellular telephone, personal cellular telephone, and email address.

The directory database allows for the collection of pertinent data about a provider's organizational structure and about the details of the capabilities and contacts in a searchable and sortable format (e.g., the provider's representatives, agents or proxies). For each provider agent, the directory database hosts a plurality of fields sufficient to categorize data that may prove useful in operating the communications network, including, provider agent telephone numbers and/or telephone extensions, and the telephone numbers to which the agent would like to potentially forward calls. The database's directory can be populated by the provider on a continuing basis, sent directly to the provider and then returned by the provider via FTP, or delivered from the provider to the administrator of the directory database via e-mail or PFI. It is also possible for the provider to link a provider maintained directory database to the directory database of the system, allowing interaction between the provider directory database and the system directory database via FFI, wherein the system directory database is utilized during periods when the FFI communications system is down for any reason.

The directory database layout may be easily adapted to accommodate the needs of a particular provider. A number of sample layouts for the database directory are given below in Tables 1-5. Table 1 demonstrates a database table structure that provides for a series of entry fields identifying the accessed originating telecommunications connections (incoming telecommunications nodes), and an identifier of that node connection. Thus for each incoming telecommunications node, a record is provided that includes at a minimum, the identifier of the originating connection (I.e. a telephone number), and an identifying descriptor of that originating connection (I.e. a service provider toll free customer service number).

TABLE 1

| Field Name | Field Descriptor | Length | Description |
| --- | --- | --- | --- |
| Originating telephone Number | Alphanumeric | 15 | Telecommunications connection information for incoming telecommunications node for service provider |
| Name of person/location (other desired fields) | Alphanumeric | 50 | |

Table 2 demonstrates a database table structure that provides for a series of entry fields identifying the designated destination(s) (service provider nodes), and an identifier of that node connection. Thus for each designated destination, a record is provided that includes at a minimum, the identifier of the service provider destination node (i.e. a telephone number), an identifying descriptor of that destination connection (i.e. a provider agent telephone number), and other fields at the option of the provider, such as a connection priority designation.

TABLE 2

| Field Name | Field Descriptor | Length | Description |
| --- | --- | --- | --- |
| Forward-to-phone Numbers or phone Numbers/extensions | Alphanumeric | 15 | Telecommunications connection information for service provider destination node |
| Name of person/location | Alphanumeric | 50 | |
| Connection priority | Numeric | 1 | Relative priority of identified connection |

Table 3 demonstrates a database table structure that provides for a series of entry fields identifying the email address of a provider agent or shared provider mailbox to which voicemail audio files are to be forwarded and an identifier of that node connection. Thus for each designated voicemail destination, a record is provided that includes the identifier of the service provider destination node (I.e. an email address) and an identifying descriptor of that destination connection (I.e. a provider agent shared mailbox).

TABLE 3

| Field Name | Field Descriptor | Length | Description |
|---|---|---|---|
| Voicemail forward-to e-mail address | Alphanumeric | 50 | Service provider destination node |
| Name of person/location | Alphanumeric | 50 | Identifying descriptor of that destination connection |

Table 4 demonstrates a series of rules established for populating the directory database, so that the database may be properly interpreted by the CCR 15 system.

TABLE 4

| | |
|---|---|
| SPECIAL CHARACTERS TO BE LEFT IN TACT: (IF APPLICABLE) | "x" for extensions in phone number fields _=.@ and any other symbols specified in RFC 2822 for e-mail addresses |
| UNIQUE FIELD: HEADER/END RECORDS, RECORD LENGTH, BLOCK SIZE LAYOUTS: | Alphanumeric |

As shown in Table 6, a variety of personnel skills and priority criteria can be predetermined to allow the provider to determine before a crisis occurs the capabilities of personnel that may be available to perform job functions. Each provider agent that is available for accepting incoming calls can be prioritized based on the skills each said agent possesses. If the database record for a given provider agent identifies a number of personal attributes, skill sets, responsibility levels or other attributes, available nodes can be sorted in priority according to the best fit, i.e. highest attribute score, to determine the hierarchical order of provider nodes to which incoming contacts are directed. As part of regular evaluations of employees, different attributes may be added to the database by creating additional fields, existing attribute scores may be changed to reflect current capabilities, and relative 5 priority of job descriptions evaluated for current relevance. Most large organizations create an actual or de facto organizational chart, with said chart providing identification of job responsibilities and a chain of reporting those responsibilities. Furthermore, many organizations provide their employees with a job code, describing their particular job requirements and cross job capabilities. Such job descriptor codes are available from a number of sources, including the United States Bureau of labor statistics.

Table 5 demonstrates a database table structure that provides for a series of entry fields including an identifier of the provider agent, selected scored personal attributes, and designated destination node information for that provider agent. Thus for each provider agent to be priority scored according to the threaded communications tree, a record is provided that includes the information necessary to provide a priority score for the selected provider agent destination nodes, and other fields at the option of the provider.

TABLE 5

| FIELD NAME | FIELD DESCRIPTOR | LENGTH | DESCRIPTION |
|---|---|---|---|
| Name or department of provider agent | Alphanumeric | 15 | |
| Provider agent capability code | Alphanumeric | 50 | Coded capabilities based on personal attribute database entries |
| Calculated connection priority | Numeric | 2 | Relative priority of identified connection |
| Forward-to-phone Numbers or phone Numbers/extensions | Tab delimited alphanumeric | 50 | Telecommunications connection information for given service provider destination node, ordered in priority and tab separated. |

Table 6 shows the hypothetical attributes of key personnel for a hypothetical electric utility. Other organizations in other industries can determine which attributes are important for consideration in a crisis response plan and create a "scoring" system that reflects the organizational requirements. The field labeled "* . . . is a coded entry identifying a personnel attribute. Each scored attribute is given a score approximating the relative capability of a given provider agent to carry out the scored process. The database may also be populated with a descriptor field that allows human relations administrators or agent supervisors to update scores for particular attributes in near or actual real-time, during a crisis.

TABLE 6

Personnel attribute priority scoring

| * | Personnel Attribute Descriptor | Score Range | Description |
|---|---|---|---|
| A | Attendance | 0-4 | Attendance: relative ability of employee to perform job functions, where 0 = unavailable; 1 = available at diminished capacity at distant location; 2 = available at distant location; 3 = present at work location, diminished capacity; 4 = full capability at normal work location. |
| M | Mobility | 0-5 | Capability of employee to travel to locations away from residence. 0 = unable to travel 1-4 = relative diminished mobility; 5 = full mobility with transportation |
| S | Supervisory Level | 1-100 | Existing supervisory capacity of employee, relative to number supervised. |
| C | Customer service | 0-2 | |
| F | Financial and accounting | 0-2 | |
| G | Production or generation | 0-5 | |
| R | Maintenance and repair | 0-5 | Capability of agent to perform given maintenance and repair tasks 0 = no skills 1 = limited general skills 2 = generation system skills 3 = high voltage transmission trained; |

TABLE 6-continued

Personnel attribute priority scoring

| Personnel Attribute * Descriptor | Score Range | Description |
|---|---|---|
| | | 4 = distribution line training; 5 = fully skilled in maintenance and repair. |
| P Operations | 0-5 | |
| E Executive | 0-2 | Authorization and ability to make executive decisions. 0 = no such authority; 1 = limited authority; 2 = general authority. |

For an electric utility preparing for a pandemic situation, the ability of employees to perform their job functions may vary based on the employee's health or their responsibility to care for others. Thus, a scaled attendance factor would allow prioritized sorting based on the projected capabilities of the employees. It is presumed that supervisory employees, or the employees themselves would regularly report their attendance score to the directory database, either manually or through a remote interface. Presumably, the attendance score would default to a "0" if no report of the attendance of the employee was received, so that incapacitated employees would not be included in the threaded communications tree. The ability of an employee to travel to their normal work location is somewhat dependent on their job responsibilities, wherein customer service representatives may be fully capable of performing their job functions at their residence, executive and finance agents less efficient, and repair and maintenance personnel having an absolute requirement to be able to get to company vehicles in order to perform their assignments. Rapid assessment by an administrator of an employee's relative ability to supervise others may be necessary when absenteeism reaches high levels. Particular specialized skills may need to be individually assessed, as in Table 6 for the hypothetical electric utility, such as capabilities in customer service, financials and accounting, production or generation, maintenance and repair, and operations and executive management being separately scored.

Once the particular attributes of an employee agent are identified and entered into the directory database, contact information for the employees can be included, in a preferred embodiment, for up to five different contacts for each provider agent node or identified employee. Collating this directory information into a record display summary for an eight employee operation is presented in Table 7.

The routing administrator or crisis management planners at a service provider can determine the best priority routing for its agents prior to the occurrence of a crisis. In addition, in the case where a crisis manager or company supervisor recognizes that critical needs of the organization are not being met, the manager can update priority routing protocol (priority routing algorithm) in order to direct incoming telecommunications traffic to available agents best able to complete the necessary tasks. Referring to Table 8, a number of hypothetical algorithms can be provided for a hypothetical electric utility operations such as one with the personnel listed in Table 7.

TABLE 8

Priority routing algorithms

| # | Routing job description | Fields | Algorithm Descriptors |
|---|---|---|---|
| 010 | Customer service agents available at normal job location with supervisory capability. | AMSC | Agent must be available; Mobility desired, but not essential; Supervisory experience desired; Customer service experience required. Priority sort employees available for A > 0, M > 2, S = any, C > 0, according to [Score = (S + (M * 5) + (C * 100))] |
| 012 | Accounting executive to make important financial decisions. | AMFE | Agent must be available; Mobility desired, but not critical; Supervisory experience not relevant Financial/accounting experience required; Executive capacity priority. Priority sort employees available for A > 0, M > 0, F > 0, according to [Score = ((A * 10) + (M * 5) + (F * 100) + E * 50)] |
| 015 | Lineman to undertake repairs to distribution lines | AMSR | Agent must be available; Full mobility desired; Supervisory experience desired; Distribution repair experience required. Priority sort employees available for A > 0, M > 3, S = any, R = 4, 5, according to [Score = ((M * 5) + S)] |
| 017 | Operations crew for power generating equipment | AMSG | Agent must be available at work location; Mobility desired; Supervisory experience priority; Full skills with generation equipment. Priority sort employees available for A > 0, M > 3, S = any, G = 5, according to [Score = ((A * 10) + (M * 5) + S * 10)] |

Applying the routing code algorithm 010 from Table 8 to the personnel in Table 7, according to the priority scoring

TABLE 7

Hypothetical directory record summary

| Employee/ Provider Agent | Contacts n = 1-5 | A | M | S | C | F | G | R | P | E | Num Code | Notes |
|---|---|---|---|---|---|---|---|---|---|---|---|---|
| Jim 1 | 614-555-1211 614-555-1212 jim@work.com | 4 | 4 | 100 | 1 | 1 | 1 | 2 | 2 | 2 | | |
| Ellen 2 | 614-555-1213 | 1 | 2 | 010 | 2 | 1 | 1 | 2 | 2 | 1 | | |
| Steph 3 | 614-555-1214 steph@home | 4 | 0 | 010 | 2 | 1 | 0 | 0 | 4 | 2 | | |
| Gerry 4 | 614-555-1216 614-555-1215 | 2 | 5 | 040 | 2 | 2 | 2 | 0 | 2 | 2 | | |
| Bob 5 | 614-555-1217 | 0 | 5 | 001 | 0 | 0 | 5 | 3 | 2 | 0 | | |
| Mike 6 | 614-555-1218 | 0 | 5 | 001 | 0 | 0 | 5 | 3 | 2 | 0 | | |
| Joe 7 | 614-555-1219 | 3 | 5 | 002 | 0 | 0 | 3 | 4 | 4 | 1 | | |
| Eric 8 | 614-555-1220 | 4 | 5 | 005 | 1 | 0 | 4 | 5 | 5 | 1 | | | wherein the Score=(S+(M*5)+(e*100)), produces the following threaded routing tree in Table 9.

TABLE 9

Threaded routing tree for Routing Code 010

| Employee/<br>Provider Agent | Contacts<br>n = 1-5 | A | M | S | C | F | G | R | P | E | Score |
|---|---|---|---|---|---|---|---|---|---|---|---|
| Gerry 4 | 614-555-1216<br>614-555-1215 | 2 | 5 | 040 | 2 | 2 | 2 | 0 | 2 | 2 | 265 |
| Ellen 2 | 614-555-1213 | 1 | 2 | 010 | 2 | 1 | 1 | 2 | 2 | 1 | 220 |
| Jim 1 | 614-555-1211<br>614-555-1212<br>jim@work.com | 4 | 4 | 100 | 1 | 1 | 1 | 2 | 2 | 2 | 220 |
| Steph 3 | 614-555-1214<br>steph@home | 4 | 0 | 010 | 2 | 1 | 0 | 0 | 4 | 2 | 210 |
| Eric 8 | 614-555-1220 | 4 | 5 | 005 | 1 | 0 | 4 | 5 | 5 | 1 | 130 |
| Joe 7 | 614-555-1219 | 3 | 5 | 002 | 0 | 0 | 3 | 4 | 4 | 1 | 27 |
| Bob 5 | 614-555-1217 | 0 | 5 | 001 | 0 | 0 | 5 | 3 | 2 | 0 | 26 |
| Mike 6 | 614-555-1218 | 0 | 5 | 001 | 0 | 0 | 5 | 3 | 2 | 0 | 26 |

Agents Gerry 4, Ellen 2, Jim 1, Steph 3, Eric 8, Joe 7, Bob 5, and Mike 6 are all believed to be capable of providing customer service, according to their availability and known capabilities. Agents Joe7, Bob5, and Mike6 are either unavailable, or incapable of performing the customer service functions required. Thus, according to the routing schedule, the telecommunications contacts would be called in the order listed in Table 10.

TABLE 10

| 1 | 614-555-1216 |
| 2 | 614-555-1215 |
| 3 | 614-555-1213 |
| 4 | 614-555-1211 |
| 5 | 614-555-1212 |
| 6 | jim@work.com |
| 7 | 614-555-1214 |
| 8 | steph@home |
| 9 | 614-555-1220 |
| 10 | Voicemail |
| 11 | Broadcast message |
| 12 | Disconnect |

Figure 4:
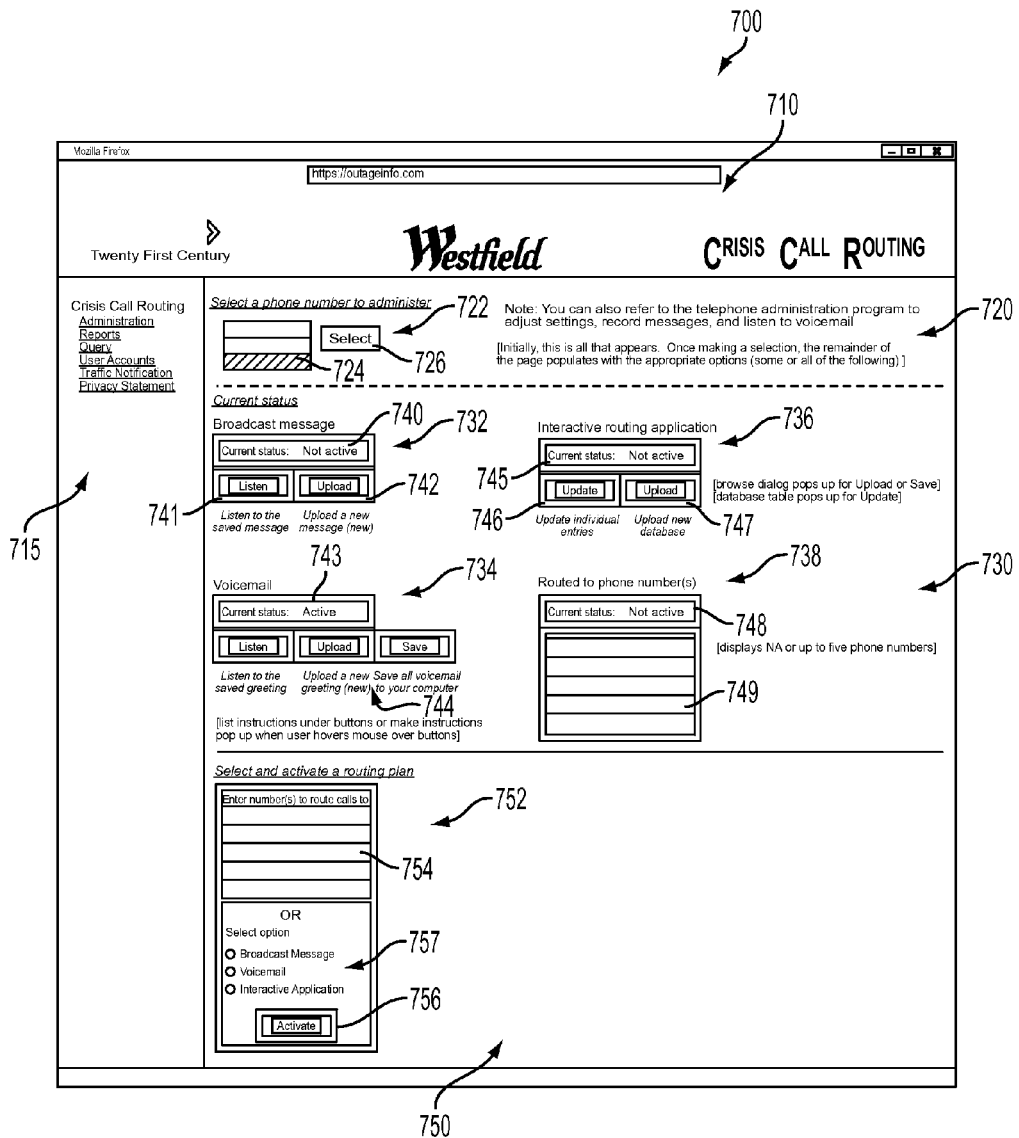
FIG. 4 shows a schematic representation of the administration interface for the CCR database.

FIG. 4 shows a schematic representation of the administration interface for the CCR database. Administrator interface 700 is comprised of a header panel 710, 10 a menu panel 715, a contact node selection panel 720, a status panel 730 and a routing plan panel 750. In a preferred embodiment, the administration interface is made available through an HTTP or HTTPS Internet protocol. A provider administrator, provider agent, provider agent supervisor, or the like, accesses the administration interface, typically by entering the IP address of the administrator interface and successfully logging into the system according to the security protocol of the provider. Header panel 710 may display identifying banners, relevant high priority announcements, and access to a utility or provider system through hyperlinks. Menu panel 715 is configurable to provide hypertext links to a variety of other functions, such as detailed announcements, reports, or email clients.

Contact node selection panel 720 provides an interface through which the contact database system may be altered, i.e. administered. As shown in FIG. 4, panel 720 is configured to allow selection of particular incoming telecommunications contacts, as telephone numbers, to be administered, via drop down menu 722. Menu 722 provides for identification of a particular telephone number (incoming telecommunications node) as at 724 to be selected, via button 726. Additional panels or pop up menus can be provided to allow selection or filtering of a subset of available incoming telecommunications nodes, such as to display only incoming telecommunications nodes which are experiencing long wait times or disruption, for instance.

Status panel 730 provides an interface through which the activity of the crisis communications routing system may be administered and activity monitored. Panel 730, as embodied in FIG. 4, provides for control of a broadcast message, at panel 732, control of the voice mail module, at panel 734, control of the interactive routing plan at 736, and to display the status and destination of routed communications. Broadcast message panel 732, as embodied in FIG. 4, displays the current broadcast message status at 740, a toggle to allow monitoring of the presently stored broadcast message at 741, and a toggle to initiate upload or editing of the broadcast message at 742. The broadcast message, as described herein, may be read from a script by a voice actor, be entered as text and read by a voice generation utility, or consist of other editable information. Similarly, voicemail panel 734 allows administration of the voicemail utility of the system, with status indicator 743 indicating whether the voicemail utility is in the active state. Buttons 744 provide for control of the retrieval of voice mail messages left in connection with the contact node chosen for administration in panel 720, monitoring and editing of the voice mail greeting, and the retention of voicemails, with other options being provided for administering voicemail as required by the particular provider.

Panel 736 is provided to allow control of the activity of a given interactive routing plan, in relation to a particular routing plan chosen in panel 750. Status indicator 745 provides an indication as to whether a routing plan has been activated. Button 746 allows the updating of the routing plan in response to alteration in routing plan selection, database updates, or varying conditions. Button 747 allows for uploading of batch changes to the provider directory database as may be necessary based on the provider's business climate. Alternatively, a separate database updating utility is available to allow particular provider agents or their supervisor to manually update entries in the directory database, or for the administrator to enable batch addition, merge or replacement updates to the directory. Finally, routing display panel 738 of status panel 730 displays the activity status of directed call routing at indicator 748, and lists at box 749 a list of telecommunications contact nodes to which incoming telecommunications contacts to the selected incoming node are being directed.

Those contact nodes displayed in box 749 are the contact nodes that have been identified according the provider node priority algorithm after utilizing the threaded telecommunications switching tree determined by the algorithm selected in panel 752. The list of nodes at 749 can be sorted by a number of parameters, including, recent activity, availability, priority, and the like.

Routing plan panel 750 provides an interface through which the routing plan for provider node priority switching according to the threaded telecommunications switching tree in the provider directory database system may be altered, i.e. administered. As shown in FIG. 4, panel 752 is configured to allow selection of the particular routing plan to be administered, which allows identification of a particular routing plan (provider node priority algorithm) as at 754 to be activated, via button 756. The various pre-selected provider node priority algorithms are optionally routed for instance by responsibility thread, ability score, personal attribute score, job code, personal attribute code, responsibility code, alternate contact code, and availability code. While only one selection menu 754 is shown in FIG. 4, it will be apparent that a series of menus can be provided as required for a particular provider, in order to allow effective selection of a switching algorithm that accounts for unexpected eventualities that can be prioritized using data present in the provider directory database. Menu 757 also provides for additional options including, for example, an option to deliver a broadcast message to an incoming telecommunications contact, to direct incoming contacts to a messaging service such as voice mail, and to allow access to additional interactive applications necessary to more effectively tailor the provider node priority algorithm.

In summary, as a preferred embodiment, the administrator interface allows for changing or updating of routing plans; a temporal call routing scheduler, allowing the routing of incoming contacts to different provider nodes or different routing options based on the time of day or the day of week; establishment, review, or updating of broadcast and other messages by voice delivery, as WAY files, or by text to voice conversion; updating of the directory database; review of CDRs and other reports on the activity of the system; review of administrative activity; and activation and deactivation of features such as call forwarding, and voice mail delivery via email, for instance. Other additional panels or pop up menus can be provided to allow selection of a subset of available provider nodes; filtering of said nodes can further be accommodated—to display only cellular telephone numbers, or email addresses, for instance.

Figure 5:
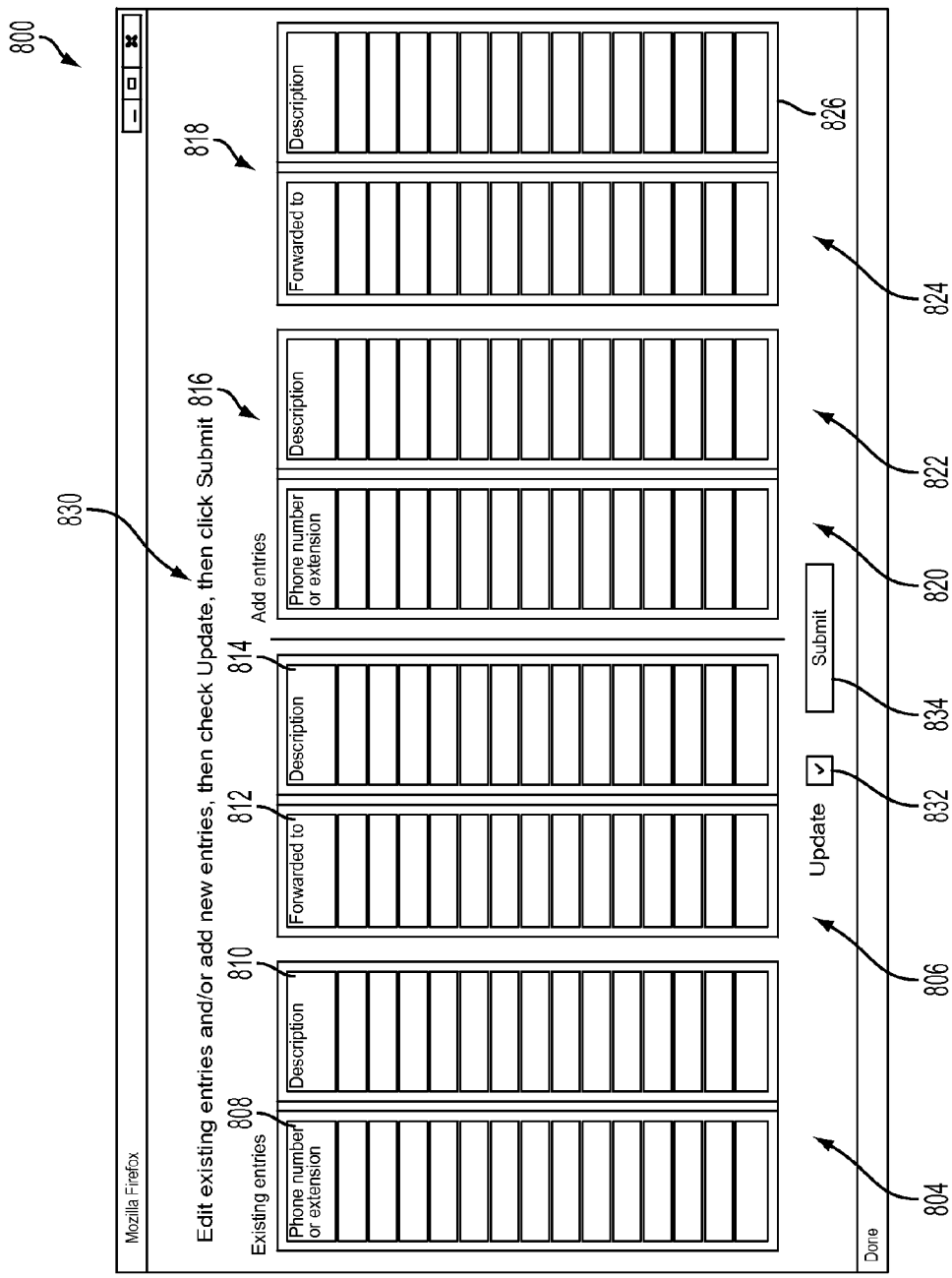
FIG. 5 shows a sample web browser based administrator interface.
Figure 6A:
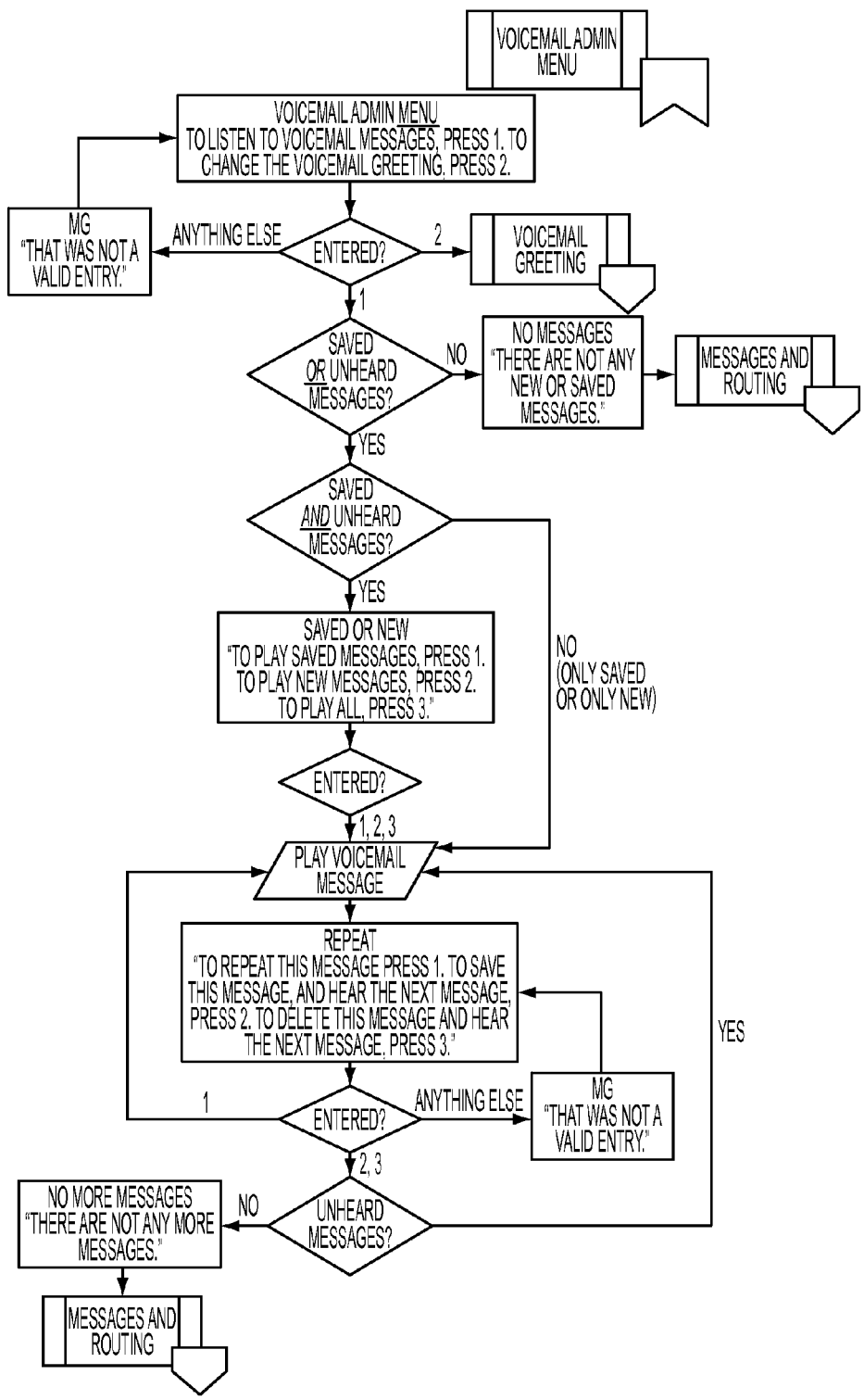
FIG. 6 shows the protocol for administration of the voicemail system for utilization with the CCR system.
Figure 6B:
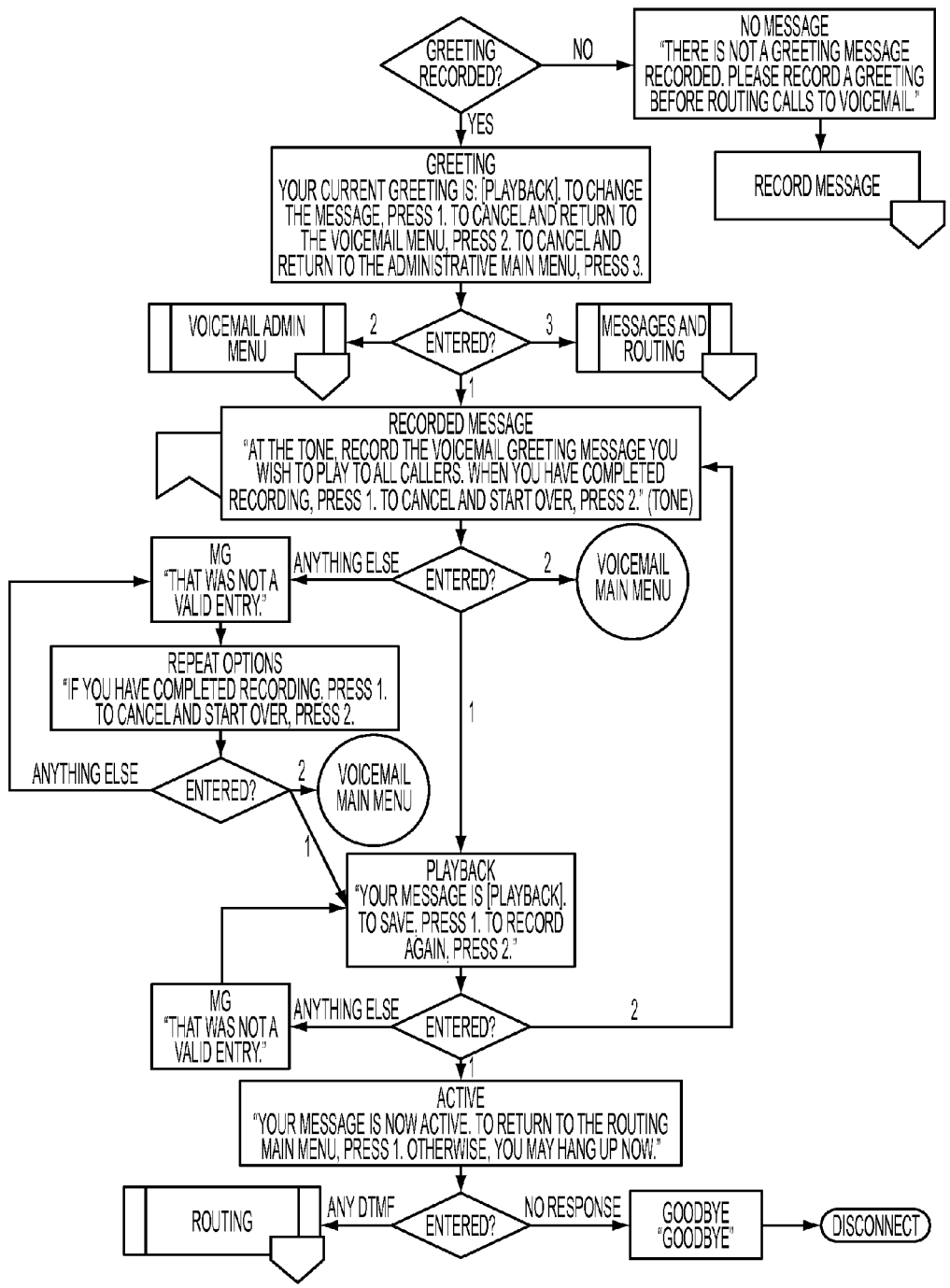

FIG. 5 shows a sample web browser based administrator interface, 800. The interface 800 provides a list of currently stored incoming telecommunications nodes along with their descriptions at 830, with column 808 listing the specific node contact information, and the corresponding fields in column 810, listing identifying characteristics for the particular incoming nodes (such as stored in the directory database, as described with respect to Table 2). The corresponding telecommunications destinations are shown at 812, representing the destination incoming calls to a particular contact number are to be routed, along with a descriptor of the destination at column 814. Interface 800 provides for an authenticated administrator to add additional incoming telecommunications nodes along with their descriptions at 816, with column 820 listing the specific node contact information, and the corresponding fields in column 822, listing identifying characteristics for the particular incoming nodes. The administrator can also add the corresponding destinations as in destination panel 818, allowing the identification of the forwarded destination to which incoming calls directed to a particular contact number are to be routed in column 824, along with a descriptor of the destination at column 826. FIGS. 6A-B show the protocol for administration of the voicemail system for utilization with the CCR system.

While the invention has been described with reference to preferred embodiments, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Since certain changes may be made in the above system without departing from the scope of the invention herein involved, it is intended that all matter contained in the above descriptions and examples or shown in the accompanying drawings shall be interpreted as illustrative and not in a limiting sense. Also, all citations referred herein are expressly incorporated herein by reference. All terms not specifically defined herein are considered to be defined according to Webster's New Twentieth Century Dictionary Unabridged, Second Edition. The disclosures of all of the citations provided are being expressly incorporated herein by reference. The disclosed invention advances the state of the art and its many advantages include those described and claimed.

What is claimed :

1. A system, comprising:
a provider directory database populated with a threaded telecommunications switching tree and accessible to a crisis communications router;
a network connection accessible to one or more incoming telecommunications nodes;
a call transfer interface for connecting the network connection with the incoming telecommunications nodes to a call transfer module capable of communicating with the incoming telecommunications nodes;
a distributed communications network of two or more provider nodes interfacing with the call transfer module through a crisis communications router, the crisis communications router connected to the call transfer module; and
provider nodes connected to the distributed telecommunications network, said provider nodes connected to the incoming telecommunications nodes through the crisis communications router connected to the call transfer module connected to the call transfer interface and routed by the crisis communications router in accordance with a provider node priority;
wherein an incoming telecommunication contact from at least one of the incoming telecommunication nodes is connected to an available telecommunication provider at a provider node after the crisis communications router determines that a telecommunication provider is predicted to be available at the provider node.

2. The system of claim 1, wherein the provider directory database further comprises one or more of a job code, a personal attribute code, a skill code, a responsibility code, an alternate contact code, and an availability code.

3. The system of claim 1, wherein the threaded switching tree is threaded according to a priority system.

4. The system of claim 1, wherein each provider node, has a database entry indicating an availability code and a responsibility code for said node.

5. The system of claim 4, wherein the incoming telecommunications contacts are connected to a selected provider node if said node is available.

6. The system of claim 4, wherein if said node is not available, an alternative telecommunications node is queried based on the responsibility code.

7. The system of claim 6, wherein if no priority switching protocol is available, the database is searched for an available alternative telecommunications node with a largest personal attribute code score.

8. The system of claim 1, wherein the provider node priority is determined by reference to the threaded telecommunications switching tree in the provider directory database.

9. The system of claim 1, wherein the telecommunication provider is predicted to be available at the given provider node in accordance with the provider node priority of the threaded telecommunications switching tree.

10. A system, comprising:
- a database populated with a switching tree and accessible to a router;
- a connection accessible to one or more incoming nodes;
- a call transfer interface for connecting the connection with the incoming nodes to a call transfer module capable of communicating with the incoming nodes;
- a distributed network of two or more provider nodes interfacing with the call transfer module through the router, the router connected to the call transfer module; and
- provider nodes connected to the distributed network, said provider nodes connected to the incoming nodes through the router connected to the call transfer module connected to the call transfer interface and routed by the router in accordance with a provider node priority;
- wherein an incoming contact from at least one of the incoming nodes is connected to an available provider at a provider node after the router determines that a provider is predicted to be available at the provider node.

11. The system of claim 10, wherein the database further comprises one or more of a job code, a personal attribute code, a skill code, a responsibility code, an alternate contact code, and an availability code.

12. The system of claim 10, wherein the switching tree is threaded according to a priority system.

13. The system of claim 10, wherein each provider node, has a database entry indicating an availability code and a responsibility code for said node.

14. The system of claim 13, wherein the incoming contacts are connected to a selected provider node if said node is available.

15. The system of claim 13, wherein if said node is not available, an alternative node is queried based on the responsibility code.

16. The system of claim 15, wherein if no priority switching protocol is available, the database is searched for an available alternative node with a largest personal attribute code score.

17. The system of claim 10, wherein the provider node priority is determined by reference to the switching tree in the database.

18. The system of claim 10, wherein the provider is predicted to be available at the given provider node in accordance with the provider node priority of the switching tree.

19. A system, comprising:
- a connection accessible to one or more incoming nodes;
- a call transfer interface for connecting the connection with the incoming nodes to a call transfer module capable of communicating with the incoming nodes;
- a distributed network of two or more provider nodes interfacing with the call transfer module through a router, the router connected to the call transfer module; and
- provider nodes connected to the distributed network, said provider nodes connected to the incoming nodes through the router connected to the call transfer module connected to the call transfer interface and routed by the router in accordance with a provider node priority;
- wherein an incoming contact from at least one of the incoming nodes is connected to an available provider at a provider node after the router determines that a provider is predicted to be available at the provider node.

* * * * *